United States Patent
Dang et al.

(10) Patent No.: US 10,892,643 B2
(45) Date of Patent: Jan. 12, 2021

(54) FACILITATION OF CHARGE OF AND COMMUNICATION WITH AN ELECTRONIC DEVICE

(71) Applicant: International Business Machines Corporation, Armonk, NY (US)

(72) Inventors: Bing Dang, Chappaqua, NY (US); Duixian Liu, Scarsdale, NY (US); Jean-Olivier Plouchart, New York, NY (US); John Knickerbocker, Orange, NJ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 356 days.

(21) Appl. No.: 15/920,803

(22) Filed: Mar. 14, 2018

(65) Prior Publication Data
US 2019/0288540 A1    Sep. 19, 2019

(51) Int. Cl.
*H02J 50/00*  (2016.01)
*H04B 1/3827*  (2015.01)
(Continued)

(52) U.S. Cl.
CPC .............. *H02J 50/005* (2020.01); *A61L 2/04* (2013.01); *A61L 2/10* (2013.01); *A61L 2/16* (2013.01);
(Continued)

(58) Field of Classification Search
CPC .. H02J 7/025; H02J 50/90; H02J 50/80; H02J 50/10; H02J 3/382; H02J 50/40;
(Continued)

(56) References Cited

U.S. PATENT DOCUMENTS 8,427,101 B2 *   4/2013   Saunamaki   ............. H02J 7/025
                                                    320/108
9,229,248 B2     1/2016   Kokonaski et al.
(Continued)

FOREIGN PATENT DOCUMENTS

WO   2008109867 A2   9/2008
WO   2010080999 A1   7/2010

OTHER PUBLICATIONS

Pandey et al., A Fully Integrated RF-Powered Contact Lens With a Single Element Display, IEEE Transactions on Biomedical Circuits and Systems, Dec. 2010, pp. 454-461, vol. 4, No. 6.
NG, Embedded Power Active Contact Lens, May 2015, 119 Pages.

*Primary Examiner* — M Baye Diao
(74) *Attorney, Agent, or Firm* — Amin, Turocy & Watson, LLP

(57) ABSTRACT

Systems, devices, and techniques facilitating wirelessly charging and/or communicating with one or more electronic devices (e.g., electronic wearable devices) are provided. A device can comprise a memory and a storage component that can be operatively coupled to the memory. The storage component can comprise one or more recesses that can receive a second device that can be charged by the storage component. The storage component can comprise a charging circuit and an inductive circuit that can be coupled to the charging circuit. The storage component can harvest energy from one or more energy sources to charge the charging circuit. Based on the energy harvested, the inductive circuit can inductively couple to the second device having a second inductive circuit and positioned in at least one of the recesses and the inductive circuit can charge a power source of the second device.

17 Claims, 11 Drawing Sheets

(51) Int. Cl.
*H02J 50/10* (2016.01)
*H02J 50/80* (2016.01)
*H02J 50/90* (2016.01)
*H02J 50/40* (2016.01)
*A61L 2/26* (2006.01)
*A61L 2/10* (2006.01)
*A61L 2/04* (2006.01)
*A61L 2/16* (2006.01)

(52) U.S. Cl.
CPC ............... *A61L 2/26* (2013.01); *H02J 50/10* (2016.02); *H02J 50/40* (2016.02); *H02J 50/80* (2016.02); *H02J 50/90* (2016.02); *H04B 1/385* (2013.01)

(58) Field of Classification Search
CPC .... H02J 50/20; A61L 2/16; A61L 2/04; A61L 2/10; A61L 2/26; A61L 2202/14; H04B 1/385
USPC .......................................................... 320/101
See application file for complete search history.

(56) References Cited

U.S. PATENT DOCUMENTS

| | | | |
|---|---|---|---|
| 9,459,469 B2 | 10/2016 | Markus et al. | |
| 9,576,168 B2 | 2/2017 | Otis et al. | |
| 9,577,437 B2* | 2/2017 | Fells | H02M 3/28 |
| 9,647,725 B1* | 5/2017 | Gay | H02J 50/80 |
| 9,673,634 B2* | 6/2017 | Baarman | H02J 7/0027 |
| 9,678,361 B2 | 6/2017 | Biederman | |
| 10,164,468 B2* | 12/2018 | Fitzgerald | H02J 50/10 |
| 10,277,055 B2* | 4/2019 | Peterson | H02J 50/10 |
| 10,286,786 B2* | 5/2019 | Geyer | B60L 53/12 |
| 2010/0259107 A1 | 10/2010 | Kinget et al. | |
| 2012/0140167 A1 | 6/2012 | Blum | |
| 2013/0194540 A1 | 8/2013 | Pugh et al. | |
| 2017/0075140 A1 | 3/2017 | Hillis et al. | |
| 2017/0095667 A1* | 4/2017 | Yakovlev | A61N 2/006 |
| 2017/0173344 A1 | 6/2017 | Campin et al. | |
| 2017/0237466 A1* | 8/2017 | Carr | H02J 7/025 455/41.1 |
| 2017/0293161 A1 | 10/2017 | Etzkorn et al. | |
| 2018/0166906 A1* | 6/2018 | Malhotra | H02J 50/50 |
| 2019/0222032 A1* | 7/2019 | Bruch | H02J 7/0013 |

\* cited by examiner

US 10,892,643 B2

FACILITATION OF CHARGE OF AND COMMUNICATION WITH AN ELECTRONIC DEVICE

BACKGROUND

The subject disclosure relates to charging and communicating with an electronic device, and more specifically, to charging of and communicating with an electronic device.

SUMMARY

The following presents a summary to provide a basic understanding of one or more embodiments of the invention. This summary is not intended to identify key or critical elements, or delineate any scope of the different embodiments or any scope of the claims. Its sole purpose is to present concepts in a simplified form as a prelude to the more detailed description that is presented later. In one or more embodiments described herein, devices, computer-implemented methods, and/or systems that facilitate wirelessly charging and communicating with an electronic device are described. In some embodiments, the electronic device can be an electronic wearable device.

According to an embodiment, a device can comprise a memory and a storage component that can be operatively coupled to the memory. The storage component can comprise one or more recesses that can receive a second device that can be charged by the storage component. The storage component can comprise a charging circuit and an inductive circuit that can be coupled to the charging circuit. The storage component can harvest energy from one or more energy sources to charge the charging circuit. Based on the energy harvested, the inductive circuit can inductively couple to the second device having a second inductive circuit and positioned in at least one of the recesses and the inductive circuit can charge a power source of the second device.

According to another embodiment, a computer-implemented method can comprise harvesting energy, by a storage device comprising a processor, from one or more energy sources. The computer-implemented method can also comprise charging, by the storage device, a circuit coupled to the storage device based on harvested energy. The circuit can be coupled to an inductive coil. The computer-implemented method can further comprise charging, by the storage device, a power source of a second device based on inductively coupling, by the storage device, the inductive coil of the storage device with a second inductive coil of the second device.

According to a further embodiment, a system can comprise a first device that can have an inductive circuit and a second device that can have a storage component that can comprise a second inductive circuit that can inductively couple to the inductive circuit of the first device. The second device can comprise a recess that can receive the first device that can be charged by the storage component. The storage component can comprise a charging circuit that can be charged based on harvested energy by the storage component from one or more energy sources. The inductive coupling between the inductive circuit and the second inductive circuit can charge a power source of the first device.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Figure 1:
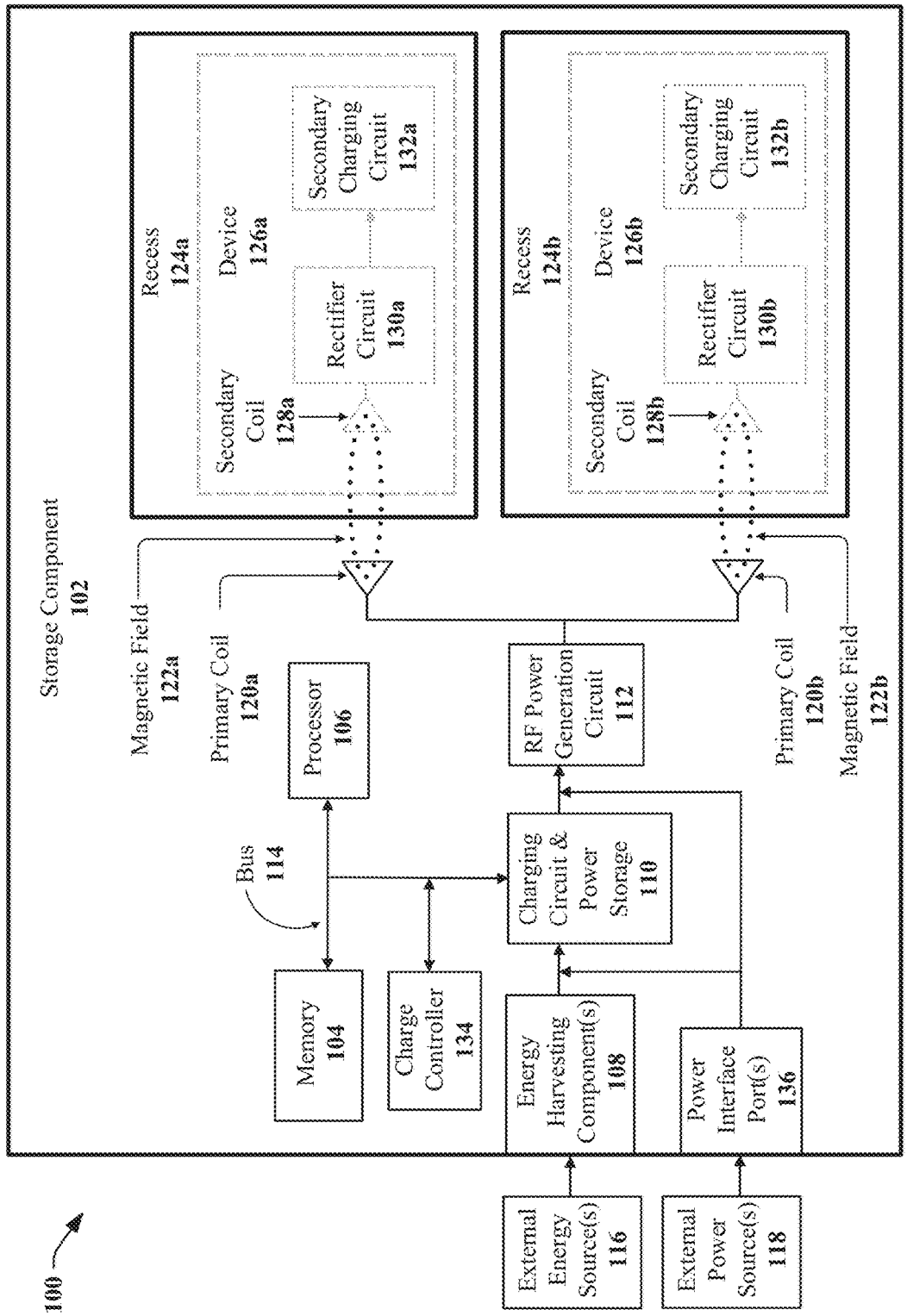
FIG. 1 illustrates a block diagram of an example, non-limiting system 100 that facilitates wirelessly charging one or more electronic devices in accordance with one or more embodiments of the disclosed subject matter.

Turning now to the drawings, FIG. 1 illustrates a block diagram of an example, non-limiting system 100 that facilitates wirelessly charging one or more electronic devices in accordance with one or more embodiments of the disclosed subject matter. In some embodiments described herein, the electronic devices can be or include electronic wearable devices. In the embodiment shown in FIG. 1, the system 100 can comprise storage component 102. According to several embodiments, the storage component 102 can comprise memory 104, processor 106, one or more energy harvesting components 108, charging circuit and power storage 110, radio frequency (RF) power generation circuit 112, bus 114, one or more primary coil 120a, 120b, one or more recess 124a, 124b, charge controller 134, and/or one or more power interface ports 136.

Although the system 100 and/or the storage component 102 can comprise the components indicated above, it should be appreciated that the embodiment shown in FIG. 1 is for illustration only, and as such, the architecture of the system 100 and/or the storage component 102 is not so limited. For instance, according to several embodiments, the system 100 and/or the storage component 102 can further comprise various computer and/or computing-based elements described herein with reference to operating environment 1100 and FIG. 11. In several embodiments, such computer and/or computing-based elements can be used in connection with implementing one or more of the systems, devices, and/or components shown and described in connection with FIG. 1 or other figures disclosed herein. For instance, the system 100 and/or the storage component 102 can comprise and/or be coupled to (e.g., communicatively, electrically, operatively, etc.) to various computer hardware and/or software components, such as input/output ports and/or interfaces, communication connections and/or interfaces, input/output components (e.g., a mouse, a keyboard, a display monitor, one or more speakers, etc.), an operating system, and/or one or more software applications suitable for implementing one or more of the systems, devices, and/or components shown and described in connection with FIG. 1 or other figures disclosed herein.

The memory 104 can store one or more computer and/or machine executable components and/or instructions that, when executed by the processor 106, can facilitate performance of operations defined by the executable component(s) and/or instruction(s). For example, the memory 104 can store computer and/or machine executable components and/or instructions that, when executed by the processor 106, can facilitate execution of the various functions described herein relating to the energy harvesting components 108, the charging circuit and power storage 110, the RF power generation circuit 112, and/or the charge controller 134.

In several embodiments, the memory 104 can comprise volatile memory and/or non-volatile memory that can employ one or more memory architectures. In some embodiments, such volatile memory can act as external cache memory and/or can comprise random access memory (RAM), static RAM (SRAM), dynamic RAM (DRAM), synchronous DRAM (SDRAM), double data rate SDRAM (DDR SDRAM), enhanced SDRAM (ESDRAM), and/or the like. Examples of non-volatile memory can comprise read only memory (ROM), programmable ROM (PROM), electrically programmable ROM (EPROM), electrically erasable programmable ROM (EEPROM), Flash memory, 3D Flash memory, and/or resistive memory, such as resistive random access memory (RRAM). In several embodiments, such volatile and/or non-volatile memory can employ one or more memory devices (e.g., magnetic disk drive, solid state disk (SSD), flash memory card, memory stick, a compact disk ROM device (CD-ROM), CD recordable drive (CD-R Drive), CD rewritable drive (CD-RW Drive), digital versatile disk ROM drive (DVD-ROM), and/or the like). In some embodiments, non-volatile memory can comprise computer memory (e.g., physically integrated with the system 100 and/or the storage component 102 or a mainboard thereof). In other embodiments, non-volatile memory can comprise removable memory (e.g., a secure digital (SD) card, a compact Flash (CF) card, a universal serial bus (USB) memory stick, and/or the like).

According to some embodiments, the processor 106 can comprise one or more types of processors and/or electronic circuitry that can implement one or more computer and/or machine executable components and/or instructions that can be stored on the memory 104. For example, the processor 106 can perform various operations that can be specified by such computer and/or machine executable components and/or instructions including, but not limited to, logic, control, input/output (I/O), arithmetic, and/or the like. In some embodiments, the processor 106 can comprise one or more central processing unit, microprocessor, microcontroller, System on a Chip (SOC), multi-core processor, array processor, vector processor, dual microprocessors, and/or the like.

In some embodiments, one or more of the memory 104, the processor 106, the energy harvesting components 108, the charging circuit and power storage 110, the RF power generation circuit 112, the charge controller 134, and/or the power interface ports 136 can be communicatively, electrically, and/or operatively coupled to one another via the bus 114, for example, to perform one or more functions of the system 100, the storage component 102, and/or any components coupled therewith. In several embodiments, the bus 114 can comprise one or more memory bus, memory controller, peripheral bus, external bus, local bus, and/or the like that can employ various bus architectures. Examples of such bus architectures can include, but are not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCM-CIA), Firewire (IEEE 1394), Small Computer Systems Interface (SCSI), and/or the like.

As referenced herein, components that can be "electrically" coupled can be coupled via electrical circuitry. For example, the terms "electrical circuitry," "electronic circuitry," "electric circuitry," "circuitry," and/or the like, utilized herein to describe components that can be "electrically" coupled can refer to coupling such components via one or more electronic components (e.g., resistors, transistors, capacitors, inductors, diodes, etc.) that are interconnected by conductive wires and/or traces through which electric current can flow (e.g., alternating current and/or direct current). As employed herein, the terms "electrical circuitry," "electronic circuitry," "electric circuitry," "circuitry," and/or the like, can describe one or more electric circuits that can facilitate various operations of the system 100, the storage component 102, and/or any components coupled therewith (e.g., transferring, storing, and/or altering electrical current, electrical signals, and/or electrical data).

In numerous embodiments, the storage component 102 can receive, support, and/or store one or more device 126a, 126b via the recess 124a, 124b. In several embodiments, the device 126a, 126b can comprise any type of electronic device, electroactive device, powered device, and/or the like, that can be employed, utilized or worn by an entity (e.g., an animate entity, such a human, animal, etc.) and that can comprise a power source (e.g., a rechargeable battery) that can be electrically charged to power the device components. Although the device 126*a*, 126*b* are depicted in various figures disclosed herein as one or more contact lenses, it should be appreciated that the embodiments shown in such figures are for illustration only, and as such, the various systems, devices, components, and/or processes of the subject disclosure are not so limited. For example, the device 126*a*, 126*b* can comprise one or more electronic devices including, but not limited to, fingernail sensor, contact lens (e.g., ophthalmic lens, contact lens, intraocular lens, ocular lens, etc.), finger ring sensor, wearable sensor, and/or the like. In several embodiments, the device 126*a*, 126*b* can comprise one or more devices that can be temporarily employed by an entity (e.g., removable devices, such as electronic ophthalmic lenses, contact lenses, artificial fingernails, accessories, rings, bracelets, necklaces, watches, glasses, etc.). In other embodiments, the device 126*a*, 126*b* can comprise one or more devices that can be permanently employed by an entity (e.g., implanted devices, such as intraocular lens).

In several embodiments, the subject disclosure (e.g., the storage component 102) can facilitate wirelessly charging and/or communicating with (e.g., as described below) various types of the device 126*a*, 126*b* having healthcare and/or medical applications (e.g., collecting healthcare and/or medical data pertaining to the entity wearing the device). In other embodiments, the subject disclosure (e.g., the storage component 102) can facilitate wirelessly charging and/or communicating with (e.g., as described below) various types of the device 126*a*, 126*b* incorporating lenses that can be employed by (e.g., worn) and/or interface with an entity (e.g., glasses, goggles, cameras, binoculars, microscopes, and/or the like).

In numerous embodiments, the subject disclosure (e.g., the storage component 102) can facilitate a single occurrence of wireless charging and/or communication with the device 126*a*, 126*b*. In some embodiments, the subject disclosure (e.g., the storage component 102) can facilitate repeated wireless charging and/or communication with the device 126*a*, 126*b* (e.g., repeatedly charging and/or communicating with numerous quantities of the same type of device 126*a*, 126*b* and/or repeatedly charging and/or communicating with the same device 126*a*, 126*b*).

In multiple embodiments, the device 126*a*, 126*b* can comprise one or more secondary coil 128*a*, 128*b*, one or more rectifier circuit 130*a*, 130*b*, and/or one or more secondary charging circuit 132*a*, 132*b*. In FIG. 1, the device 126*a*, 126*b*, the secondary coil 128*a*, 128*b*, the rectifier circuit 130*a*, 130*b*, and the secondary charging circuit 132*a*, 132*b* are depicted with dashed lines to indicate that, according to this embodiment, these components are not part of the recess 124*a*, 124*b* or the storage component 102.

According to several embodiments, the energy harvesting components 108 can comprise one or more photovoltaic cell (e.g., a solar cell), radio frequency antenna, thermo-generator (e.g., a thermoelectric generator), microgenerator, wind turbine, ultrasonic transducer, piezoelectric generator, and/ or the like, that can harvest energy from one or more external energy sources 116. In various embodiments, the storage component 102 can comprise any of the energy harvesting component examples listed above and/or any combination thereof. In several embodiments, the energy harvesting components 108 can harvest energy from external energy sources 116 that can include, but are not limited to, magnetic energy, electric energy, electromagnetic radiant energy, solar energy, ultrasonic energy, thermal energy, kinetic energy, wind energy, light energy, ambient energy, and/or the like.

In numerous embodiments, the energy harvesting components 108 can harvest various types of energy and convert the energy to electrical energy (e.g., a direct electrical current or voltage). For example, the storage component 102 can comprise a radio frequency receiver antenna that can intercept ambient radio waves propagating through the atmosphere to capture electromagnetic radiant energy. For instance, the oscillating transverse magnetic and electric fields inherent to the radio waves can apply oscillating forces on the electrons in the atoms of the antenna material, thereby producing an alternating electric current in the antenna material (e.g., according to Faraday's law of induction). In such an example, the antenna can comprise terminals that can be electrically coupled (e.g., via electrical circuitry defined above) to a rectifier that can convert the alternating electric current to direct electric current.

In other embodiments, the storage component 102 can comprise one or more photovoltaic cells (e.g., solar cells) that can absorb light (e.g., sunlight and/or artificial light, such as light produced by a Light-Emitting Diode (LED), etc.) and convert the energy in the light to electrical energy (e.g., via the photovoltaic effect). For example, the light energy absorbed by a solar cell can excite electrons in the solar cell material to a higher-energy state, thereby creating an electric potential (e.g., a voltage) in atoms of the solar cell material, which the solar cell can convert to a direct electrical current. According to other embodiments, the storage component 102 can comprise one or more thermoelectric-generators that can convert thermal energy (e.g., energy stored in heated gas, liquid, solids, etc.) to electric energy (e.g., via the Seebeck effect, the thermoelectric effect, etc.). In still other embodiments, the storage component 102 can comprise one or more microgenerators that can covert kinetic energy (e.g., vibrations, human movement, etc.) to electric energy (e.g., via transferring the kinetic energy to an electric generator which causes the kinetic energy to induce an electrical current in a circuit, according to Faraday's law of induction).

According to numerous embodiments, the energy harvesting components 108, the charging circuit and power storage 110, the RF power generation circuit 112, the primary coil 120*a*, 120*b*, and/or the power interface ports 136 can be electrically coupled via bus 114 and/or via electrical circuitry (e.g., as defined above) that can facilitate transferring the harvested energy (e.g., the solar energy, light energy, electromagnetic radiant energy, etcetera, that can be captured and/or converted to direct current by the energy harvesting components 108). In several embodiments, the energy harvesting components 108 can transfer the harvested energy (e.g., in the form of direct current (DC)) to the charging circuit and power storage 110 (e.g., via the bus 114 and/or electrical circuitry).

In numerous embodiments, the charging circuit and power storage 110 can store the electrical energy (e.g., via storing direct current or voltage in a battery, a capacitor, and/or other storage component suitable for storing electric current or voltage). In such an example, the storing of the electrical energy (e.g., via storing voltage in a battery, such as a thin-film solid state battery) is indicative of charging the charging circuit and power storage 110. In numerous embodiments, the charging circuit and power storage 110 can further discharge and/or transfer (e.g., via the bus 114 and/or electrical circuitry) the stored electric energy to one or more components of the storage component 102 (e.g., the processor 106, the RF power generation circuit 112, the charge controller 134, etc.). For example, according to several embodiments, the charging circuit and power storage 110 can discharge and/or transfer (e.g., via the bus 114 and/or electrical circuitry) the stored electric energy to the RF power generation circuit 112, thereby effectively charging the RF power generation circuit 112. According to multiple embodiments, the charging circuit and power storage 110 can comprise a thin-film solid state battery comprising a voltage capacity ranging between 3.2 Volts (V) to 4.2 Volts (V).

According to some embodiments, the charge controller 134 can comprise a system, device, and/or electrical circuitry that can facilitate prompting the charging circuit and power storage 110 to perform various operations. For example, the charge controller 134 can comprise an application specific integrated circuit (ASIC) that can facilitate prompting the charging circuit and power storage 110 to store the electrical energy received from the energy harvesting components 108 (e.g., via charging a battery), to stop storing the energy (e.g., stop charging a battery), and/or to discharge and/or transfer (e.g., via the bus 114 and/or electrical circuitry) the stored energy in the form of a direct current to the RF power generation circuit 112. In such an example, the discharge and/or transfer of the stored energy, in the form of a direct current, to the RF power generation circuit 112 is indicative of charging the RF power generation circuit 112. In some embodiments, the memory 104 can store computer and/or machine executable components and/or instructions that, when executed by the processor 106, can facilitate the charge controller 134 prompting the charging circuit and power storage 110 to perform one or more of the operations described above (e.g., charging a battery, stop charging a battery, discharge a battery, etc.).

In various embodiments, the power interface ports 136 can comprise one or more interface ports (e.g., a USB port, a direct current power input port, etc.) that can facilitate receiving electrical energy (e.g., a direct current) from the external power sources 118. Examples of the external power sources 118 can include, but are not limited to, an AC/DC adapter that can convert an alternating current to a direct current, a battery and/or rechargeable battery storing voltage that can discharge the stored voltage in the form of direct current, an electronic device (e.g., a computing device) that can transfer direct current (e.g., via a Universal Serial Bus (USB) cable), and/or the like. In several embodiments, the external power sources 118 can couple (e.g., electrically, operatively, etc.) to the power interface ports 136 (e.g., via a Universal Serial Bus (USB) cable) to input a direct current into the charging circuit and power storage 110 and/or the RF power generation circuit 112 (e.g., via the bus 114 and/or electrical circuitry). In some embodiments, the charging circuit and power storage 110 can store the direct current received from the external power sources 118 (e.g., via storing direct current or voltage in a battery, a capacitor, and/or other storage component as described above).

In several embodiments, the RF power generation circuit 112 can convert a direct current (e.g., received from the charging circuit and power storage 110 and/or the external power sources 118) to an alternating current and/or signal (e.g., via an oscillator, an inverter, etc.) and can further transfer the alternating current to the primary coil 120a, 120b (e.g., via the bus 114 and/or electrical circuitry). In such an example, the transfer of the alternating current to the primary coil 120a, 120b is indicative of charging the primary coil 120a, 120b. In this example, the alternating current running through the primary coil 120a, 120b can generate (e.g., according to Ampere's law) an oscillating and/or rotating magnetic field, such as magnetic field 122a, 122b. Continuing with this example, the magnetic field 122a, 122b can pass through the secondary coil 128a, 128b of the device 126a, 126b and can further induce an alternating current in the secondary coil 128a, 128b (e.g., according to Faraday's law of induction). In such an example, the RF power generation circuit 112 and/or the primary coil 120a, 120b are indicative of an inductive circuit(s), and generating the magnetic field 122a, 122b that passes through and induces an alternating current in the secondary coil 128a, 128b, is indicative of inductively coupling the primary coil 120a, 120b to the secondary coil 128a, 128b. In this example, such inductive coupling is indicative of wirelessly transmitting electrical energy (e.g., electrical current) to the device 126a, 126b. It should be appreciated that such inductive coupling, as described herein, can also be referred to as near-field power transfer, inductive power transfer, nonradiative power transfer, inductive charging, wireless power transmission, and/or the like.

According to multiple embodiments, the RF power generation circuit 112 can comprise a voltage-controlled oscillator and/or a voltage-controlled oscillator circuit that can convert direct current from a power source to an alternating current and/or signal with an oscillation frequency that is controlled by a voltage input. For example, the power interface ports 136 can facilitate receiving and transferring a direct current from the external power sources 118 to the voltage-controlled oscillator circuit (e.g., via the bus 114 and/or electrical circuitry). In these embodiments, the voltage-controlled oscillator circuit can convert the direct current to an alternating current and/or signal and can further transfer the alternating current/signal to the primary coil 120a, 120b to facilitate inductively coupling the primary coil 120a, 120b to the secondary coil 128a, 128b as described above.

In numerous embodiments, the RF power generation circuit 112 can convert (e.g., via an oscillator, an inverter, etc.) a direct current to an alternating current and/or signal comprising a signal frequency ranging between 100 megahertz (MHz) to 10 gigahertz (GHz). In an embodiment, the RF power generation circuit 112 can convert (e.g., via an oscillator, an inverter, etc.) a direct current to an alternating current and/or signal comprising a signal frequency of 300 MHz.

In some embodiments, the primary coil 120a, 120b and/or the secondary coil 128a, 128b can comprise one or more inductive coils, inductive loop antennae, three-dimensional (3D) coil structures, spiral antennae, and/or other similar antennae structures suitable to facilitate inductive coupling as described above. For example, the primary coil 120a, 120b and/or the secondary coil 128a, 128b can comprise antennae structures including, but not limited to, single turn inductive loop/coil antenna, multi-turn inductive loop/coil antenna, and/or the like.

According to some embodiments, the primary coil 120a, 120b can comprise multi-turn inductive loop/coil antennae structures comprising an outer diameter ranging between 100 micrometers (μm) to 100 millimeters (mm) and/or an inside diameter ranging between 100 μm to 100 mm. In an embodiment, the primary coil 120a, 120b can comprise a single turn inductive loop/coil antennae structure comprising an outer diameter of 12 mm.

In some embodiments, the secondary coil 128a, 128b can comprise multi-turn inductive loop/coil antennae structures comprising an outer diameter ranging between 100 μm to 100 mm and/or an inside diameter ranging between 100 μm to 100 mm. In an embodiment, the secondary coil 128a, 128*b* can comprise a single turn inductive loop/coil antennae structure comprising an outer diameter of 10 mm.

In numerous embodiments, the primary coil 120*a*, 120*b* and/or the secondary coil 128*a*, 128*b* can be fabricated from one or more various suitable conductive materials and/or alloys. For example, the primary coil 120*a*, 120*b* and/or the secondary coil 128*a*, 128*b* can be fabricated from materials and/or alloys including, but not limited to, silver, copper, gold, nickel, carbon, titanium, cobalt, indium tin oxide, platinum, and/or the like.

In several embodiments, the primary coil 120*a*, 120*b* and/or the secondary coil 128*a*, 128*b* can be structured and/or configured in such a manner to facilitate optimal alignment (e.g., planar, axial, proximal, etc.) of the primary coil 120*a*, 120*b* with the secondary coil 128*a*, 128*b* and/or to facilitate optimal inductive coupling of the primary coil 120*a*, 120*b* to the secondary coil 128*a*, 128*b*. For example, the primary coil 120*a*, 120*b* can comprise a three-dimensional (3D) coil structure integrated in a surface of the recess 124*a*, 124*b* and/or wrapped or coiled around the perimeter of the recess 124*a*, 124*b*. For instance, the primary coil 120*a*, 120*b* and/or the secondary coil 128*a*, 128*b* can respectively comprise a single turn inductive coil antenna. In such an example, the primary coil 120*a*, 120*b* can comprise an inner diameter that is larger than the outer diameter of the secondary coil 128*a*, 128*b*, thereby facilitating locating the secondary coil 128*a*, 128*b* inside and immediately adjacent to the primary coil 120*a*, 120*b*. In this example, locating the secondary coil 128*a*, 128*b* inside and immediately adjacent to the primary coil 120*a*, 120*b* can facilitate optimal alignment (e.g., planar, axial, proximal, etc.) of the primary coil 120*a*, 120*b* with the secondary coil 128*a*, 128*b*.

In numerous embodiments, the storage component 102 can receive, support, and/or store one or more device 126*a*, 126*b* via the recess 124*a*, 124*b*. In some embodiments, the storage component 102 and/or the recess 124*a*, 124*b* can comprise one or more surfaces, guiding structures, support structures, and/or storing structures that can receive, guide, support, and/or store the device 126*a*, 126*b* in such a manner to facilitate optimal alignment (e.g., planar, axial, proximal, etc.) of the primary coil 120*a*, 120*b* with the secondary coil 128*a*, 128*b*. For example, one or more surfaces of the recess 124*a*, 124*b* can comprise a concave shape that can receive a corresponding convex surface of the device 126*a*, 126*b*. In another embodiment, the recess 124*a*, 124*b* can comprise a guide and/or support structure extending from a surface of the recess 124*a*, 124*b* that can receive, guide, support, and/or store the device 126*a*, 126*b*. In several embodiments, the primary coil 120*a*, 120*b*, the recess 124*a*, 124*b*, the device 126*a*, 126*b*, and/or the secondary coil 128*a*, 128*b* can be structured and/or configured in such a manner to facilitate optimal proximal alignment. For example, such components can be structured and/or configured such that the distance between the primary coil 120*a*, 120*b* and the secondary coil 128*a*, 128*b* can range between 200 µm to 2 mm.

In still other embodiments, the storage component 102, the recess 124*a*, 124*b*, and/or the device 126*a*, 126*b* can comprise one or more magnetic components (e.g., magnets, magnetic coating, magnetic paint, ferromagnetic material, etc.) that can magnetically couple the recess 124*a*, 124*b* to the device 126*a*, 126*b* and/or the storage component 102 to the device 126*a*, 126*b*. For example, the recess 124*a*, 124*b* can comprise a magnet and/or a magnetic coating or paint on an internal surface of the recess 124*a*, 124*b* that can attract a corresponding magnetic component (e.g., a magnet, ferromagnetic material, etc.) integrated in the device 126*a*, 126*b* such that the primary coil 120*a*, 120*b* aligns axially with the secondary coil 128*a*, 128*b*, thereby optimizing inductive coupling.

It should be appreciated that the various embodiments described herein related to optimally aligning the primary coil 120*a*, 120*b* with the secondary coil 128*a*, 128*b* facilitate optimal energy transmission efficiency associated with inductively coupling the primary coil 120*a*, 120*b* with the secondary coil 128*a*, 128*b*. It should also be appreciated that facilitating optimal energy transmission efficiency is indicative of facilitating optimal charging efficiency associated with inductively charging the rectifier circuit 130*a*, 130*b* and/or a power source coupled with the secondary charging circuit 132*a*, 132*b*. For example, according to numerous embodiments, the subject disclosure (e.g., the storage component 102, the charging circuit and power storage 110, the RF power generation circuit 112, and/or the primary coil 120*a*, 120*b*) can facilitate transmitting, through inductive coupling, charging power ranging between 1 microwatt (µW) to 1 watt (W). In an embodiment, the subject disclosure (e.g., the storage component 102, the charging circuit and power storage 110, the RF power generation circuit 112, and/or the primary coil 120*a*, 120*b*) can facilitate transmitting, through inductive coupling, charging power of 40 µW.

In some embodiments, the recess 124*a*, 124*b* can be structured to receive, support, and/or store the device 126*a*, 126*b*, a liquid (e.g., cleaning and/or disinfecting solution, saline solution, contact lens solution, electrolyte solution, hydrogen peroxide, water, etc.), and/or a gas (e.g., oxygen, nitrogen, etc.). In numerous embodiments, the RF power generation circuit 112 can facilitate inductively coupling, through a liquid and/or a gas, the primary coil 120*a*, 120*b* with the secondary coil 128*a*, 128*b* as described above. For example, the recess 124*a*, 124*b* can comprise the device 126*a*, 126*b* and a liquid (e.g., cleaning and/or disinfecting solution, saline solution, contact lens solution, electrolyte solution, hydrogen peroxide, water, etc.). In such an example, the storage component 102 (e.g., the RF power generation circuit 112 and/or the primary coil 120*a*, 120*b*) can facilitate inductively coupling to the device 126*a*, 126*b* (e.g., via an inductive circuit, such as the secondary coil 128*a*, 128*b* and/or the rectifier circuit 130*a*, 130*b*), through the liquid, in the same or similar manner as described above with reference to inductively coupling the primary coil 120*a*, 120*b* to the secondary coil 128*a*, 128*b*.

By way of example, not limitation, the various embodiments of the subject disclosure described herein (e.g., the storage component 102 and/or one or more components associated therewith) can be fabricated and/or manufactured utilizing one or more techniques and/or materials for printing electronic-based systems, devices, components, circuits, and/or the like. Examples of such printing techniques can include, but are not limited to: three-dimensional (3D) printing, additive manufacturing (AM), stereolithography (STL), rapid prototyping, inkjet printing, sheet-based inkjet printing, screen printing, flexography, offset printing, rotogravure printing, aerosol jet printing, maskless mesoscale materials deposition (M3D), evaporation printing, microcontact printing, and/or the like. Examples of such printing materials can include, but are not limited to: plastics, polymers, silver, copper, gold, nickel, carbon, titanium, cobalt, indium tin oxide, platinum, silicon, dielectric materials, and/or any suitable organic/inorganic and/or conductive/non-conductive materials that can be utilized with one or more of the printing techniques described above.

According to other embodiments, the storage component 102 and/or one or more of the components illustrated and/or described in connection with the storage component 102 can comprise and/or be coupled (e.g., electrically, operatively, communicatively, physically, etc.) to one or more circuit boards (e.g., analog circuit boards, digital circuit boards, integrated circuit boards, printed circuit boards, and/or the like). In some embodiments, such one or more circuit boards can comprise integrated circuit boards and/or a printed circuit boards. In these embodiments, such one or more circuit boards can be fabricated and/or manufactured utilizing various printing techniques/materials (e.g., as described above), semiconductor lithography techniques/materials (e.g., photolithography, microlithography, nanolithography, nanoimprint lithography, photoresist techniques, patterning techniques, etching techniques, etc.), and/or other suitable techniques/materials utilized to integrate electrical circuits and/or electrical components on one or more layers of substrate materials.

In multiple embodiments, the secondary coil 128a, 128b and/or the rectifier circuit 130a, 130b are indicative of an inductive circuit(s), and can be electrically coupled (e.g., via electrical circuitry) to the secondary charging circuit 132a. In some embodiments, the rectifier circuit 130a, 130b can convert the alternating current induced in the secondary coil 128a, 128b (e.g., as described above) to a direct current (e.g., via a rectifier). In several other embodiments, the rectifier circuit 130a, 130b can further facilitate transferring the direct current to the secondary charging circuit 132a, 132b (e.g., via electrical circuitry described above). In several embodiments, the secondary charging circuit 132a, 132b can store the electrical energy (e.g., via storing voltage in a capacitor and/or a battery, such as a thin-film solid state battery), which is indicative of charging the secondary charging circuit 132a, 132b and/or charging a power source (e.g., a thin-film solid state battery) of the device 126a, 126b. According to multiple embodiments, the secondary charging circuit 132a, 132b can comprise a thin-film solid state battery comprising a voltage capacity ranging between 3.2 V to 4.2 V. In an embodiment, the secondary charging circuit 132a, 132b can comprise a thin-film solid state battery comprising a voltage capacity of 3.7 V. In numerous embodiments, the secondary charging circuit 132a, 132b can further discharge and/or transfer (e.g., via electrical circuitry) the stored electric energy to one or more actuators, sensors, and/or various other electronic components that can be integrated in the device 126a, 126b.

Figure 2:
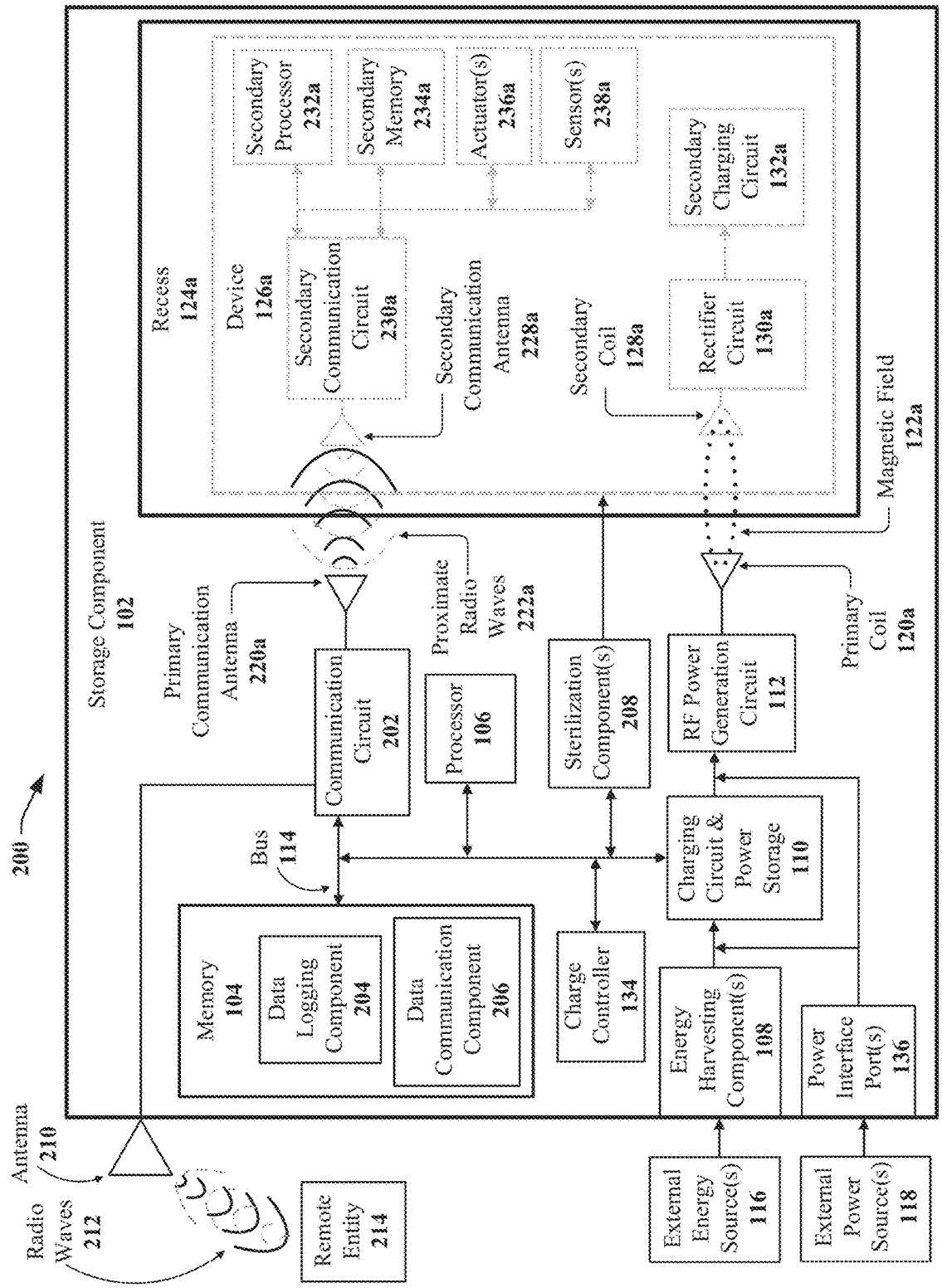
FIG. 2 illustrates a block diagram of an example, non-limiting system 200 that facilitates wirelessly charging and/or communicating with one or more electronic devices in accordance with one or more embodiments of the disclosed subject matter.

FIG. 2 illustrates a block diagram of an example, non-limiting system 200 that facilitates wirelessly charging and/or communicating with one or more electronic devices in accordance with one or more embodiments of the disclosed subject matter. In one or more embodiments, the system 200 can be a subsystem of the system 100 (e.g., the system 100 can include the system 200, and vice versa). For purposes of brevity and clarity, FIG. 2 illustrates an embodiment of the storage component 102 comprising a single primary coil 120a, a single magnetic field 122a, and a single recess 124a that can receive, support, and/or store a single device 126a. Although FIG. 2 depicts a single quantity for such components, it should be appreciated that the embodiment shown in FIG. 2 is for illustration only, and as such, the system 200 is not so limited. Repetitive description of like elements employed in respective embodiments is omitted for sake of brevity.

In the embodiment shown in FIG. 2, the system 200 can comprise the storage component 102. According to several embodiments, the storage component 102 can comprise communication circuit 202, one or more sterilization components 208, antenna 210, and/or one or more primary communication antenna 220a. As illustrated in FIG. 2, the memory 104 can comprise data logging component 204 and/or data communication component 206. Although the storage component 102 and/or the memory 104 can comprise the components indicated above, it should be appreciated that the embodiment shown in FIG. 2 is for illustration only, and as such, the architecture of the storage component 102 and/or the memory 104 is not so limited.

According to multiple embodiments, one or more of the device 126a can comprise one or more secondary communication antenna 228a, one or more secondary communication circuit 230a, secondary processor 232a, secondary memory 234a, actuators 236a, and/or sensors 238a. In FIG. 2, the device 126a and its associated components (e.g., the secondary communication antenna 228a, the secondary communication circuit 230a, the secondary processor 232a, the secondary memory 234a, actuators 236a, sensors 238a, etc.) are depicted with dashed lines to indicate that, according to this embodiment, these components are not part of the recess 124a or the storage component 102.

In some embodiments, the communication circuit 202 and/or the sterilization components 208 can be communicatively, electrically, and/or operatively coupled to one another via the bus 114, for example, to perform one or more functions of the system 200 and/or the storage component 102. In several embodiments, the communication circuit 202 can be communicatively, electrically, and/or operatively coupled to the antenna 210 and/or the primary communication antenna 220a via electrical circuitry.

In several embodiments, the communication circuit 202 and/or the secondary communication circuit 230a can comprise various components, systems, devices, and/or electrical circuitry to facilitate wirelessly transmitting and/or receiving electromagnetic communication signals, such as radio waves (e.g., proximate radio waves 222a). For example, in some embodiments, the communication circuit 202 and/or the secondary communication circuit 230a can comprise one or more transmitters, transceivers, modulators, oscillators, inverters, amplifiers, and/or the like, to facilitate transmitting radio waves carrying information. For instance, the communication circuit 202 and/or the secondary communication circuit 230a can comprise a transmitter having a modulator that can modulate (e.g., modify) one or more properties (e.g., amplitude, frequency, phase, pulse width, etc.) of an electric signal (e.g., a carrier signal) representing an electric current, thereby impressing a communication signal on the electric signal. In such an example, the communication signal can represent information to be transmitted. Continuing with this example, the transmitter can further transfer the modulated electric signal to the primary communication antenna 220a and/or the secondary communication antenna 228a, which can facilitate converting (e.g., according to Ampere's law) the electric current associated with the modulated electric signal to electromagnetic energy waves carrying the communication signal (e.g., the proximate radio waves 222a carrying the communication signal representing the information). In this example, converting the electric current to electromagnetic energy waves is indicative of wirelessly transmitting the communication signal.

In numerous embodiments, the communication circuit 202 can comprise one or more transmitters, transceivers, modulators, oscillators, inverters, amplifiers, and/or the like, that can facilitate wirelessly transmitting electromagnetic communication signals (e.g., proximate radio waves 222a) comprising a signal frequency ranging between 3 kilohertz (kHz) to 300 GHz. In an embodiment, the communication circuit 202 can comprise one or more transmitters, transceivers, modulators, oscillators, inverters, amplifiers, and/or the like, that can facilitate wirelessly transmitting electromagnetic communication signals (e.g., proximate radio waves 222a) comprising a signal frequency of 2.4 GHz.

In multiple embodiments, the primary communication antenna 220a and/or the secondary communication antenna 228a can comprise the same or similar antenna structures, configurations, dimensions, and/or materials as those described above for the primary coil 120a, 120b and/or the secondary coil 128a, 128b, respectively, with reference to FIG. 1. In several embodiments, the primary communication antenna 220a and/or the secondary communication antenna 228a can facilitate receiving the electromagnetic energy waves carrying the communication signal (e.g., the proximate radio waves 222a carrying the communication signal representing the information). For example, the proximate radio waves 222a can contact the primary communication antenna 220a and/or the secondary communication antenna 228a and can further induce an alternating current in the primary communication antenna 220a and/or the secondary communication antenna 228a (e.g., according to Faraday's law of induction). In such an example, the alternating current induced in the primary communication antenna 220a and/or the secondary communication antenna 228a can have a corresponding electrical signal that is representative of the transmitted modulated electrical signal.

According to multiple embodiments, the communication circuit 202 and/or the secondary communication circuit 230a can comprise one or more receivers, transceivers, demodulators, rectifiers, and/or the like, to facilitate receiving radio waves carrying information and extracting the information. For example, the communication circuit 202 and/or the secondary communication circuit 230a can comprise a receiver having a rectifier that can convert the alternating current to a direct current having a corresponding electrical signal that is representative of the modulated electrical signal. In such an example, the direct current electrical signal representing the modulated electrical signal can be processed by a demodulator to extract the communication signal from the modulated electrical signal, thereby extracting the information.

In several embodiments, the device 126a can comprise secondary processor 232a, secondary memory 234a, actuators 236a, and/or sensors 238a. In some embodiments, one or more of the device 126a components (e.g., the secondary communication antenna 228a, the secondary communication circuit 230a, the secondary processor 232a, the secondary memory 234a, the actuators 236, the sensors 238a, etc.) can be communicatively, electrically, and/or operatively coupled to one another via electrical circuitry to facilitate execution of one or more functions of such components and/or the device 126a. In some embodiments, one or more of the device 126a components can be disposed on an analog circuit board, integrated in a digital circuit board, and/or a combination thereof. For example, one or more of the device 126a components indicated above can be disposed on an integrated circuit board and/or a printed circuit board. In this example, such circuit boards can be produced utilizing the same or similar fabrication and/or manufacturing techniques and/or materials described above with reference to FIG. 1 (e.g., via printing techniques/materials, semiconductor lithography techniques/materials, and/or the like).

In some embodiments, the secondary processor 232a can comprise a microprocessor and/or a microcontroller. In numerous embodiments, the actuators 236a and/or the sensors 238a can comprise various systems, devices, components, and/or circuits that can execute any number of functions associated with the device 126a. Examples of such functions can include, but are not limited to, detecting and/or logging/recording healthcare and/or medical data pertaining to the entity wearing the device (e.g., heartrate, blood pressure, tear film data, etc.), correcting and/or enhancing vision (e.g., via adjusting lens magnification, adjusting lens focus, adjusting hue perceived by a wearer of the device 126a, etc.), and/or the like.

In numerous embodiments, the secondary memory 234a can comprise the same or similar memory types and/or components described above with reference to the memory 104 and FIG. 1. In several embodiments, the secondary memory 234a can store one or more computer and/or machine executable components and/or instructions that, when executed by the secondary processor 232a, can facilitate performance of operations defined by the executable component(s) and/or instruction(s). For example, the secondary memory 234a can store such components and/or instructions that, when executed by the secondary processor 232a can facilitate execution of the various functions performed by the actuators 236a and/or the sensors 238a. According to several embodiments, any information collected, detected, and/or logged by the actuators 236a and/or the sensors 238a when executing the various functions associated with the device 126a can be stored in the secondary memory 234a and/or transmitted to the memory 104 of the storage component 102. For example, the secondary communication circuit 230a can facilitate transmitting (e.g., as described above) a communication signal containing the data collected, detected, and/or logged by the device 126a components to the communication circuit 202, which can facilitate transferring such data to the memory 104 (e.g., via the processor 106 and/or the bus 114).

According to numerous embodiments, the data logging component 204 can comprise one or more computer and/or machine readable, writable, and/or executable components and/or instructions that, when executed by the processor 106, can facilitate performance of operations defined by such component(s) and/or instruction(s). For example, the data logging component 204 can comprise computer and/or machine executable components and/or instructions that, when executed by the processor 106, can facilitate the data logging component 204 logging, recording, and/or storing, to the memory 104, the data received from the device 126a components. For instance, in such an example, the data logging component 204 can write the data to a volatile memory component of the memory 104 (e.g., via the processor 106 executing the writable components and/or instructions of the data logging component 204).

In several embodiments, the data communication component 206 can comprise one or more computer and/or machine readable, writable, and/or executable components and/or instructions that, when executed by the processor 106, can facilitate performance of operations defined by such component(s) and/or instruction(s). For example, the data communication component 206 can comprise computer and/or machine executable components and/or instructions that, when executed by the processor 106, can facilitate the data communication component 206 management of communication signals and/or data that can be transmitted/received between the storage component 102 and the device 126a (e.g., as described above). For instance, the data communication component 206 can facilitate the communication circuit 202 transmitting a communication signal to the secondary communication circuit 230a, requesting the data collected, detected, and/or logged by the device 126a components. In other embodiments, the data communication component 206 can facilitate the communication circuit 202 transmitting a communication signal to the secondary communication circuit 230a, instructing one or more of the various components of the device 126a to execute one or more functions (e.g., to activate, deactivate, execute an operation, modify functionality, and/or the like).

According to still other embodiments, the data communication component 206 can comprise one or more computer and/or machine readable, writable, and/or executable components and/or instructions that, when executed by the processor 106, can facilitate management of communication signals and/or data that can be wirelessly transmitted/received, over a network, between the storage component 102 and one or more remote entity 214. For example, in several embodiments, the communication circuit 202 can facilitate wirelessly transmitting/receiving communication signals to/from the remote entity 214 (e.g., via the antenna 210 and/or the radio waves 212), over a network, in the same or similar manner as described above with reference to wirelessly transmitting/receiving communication signals between the communication circuit 202 and the secondary communication circuit 230a. In such embodiments, the data communication component 206 can facilitate reading/copying data stored in the memory 104 (e.g., data received from the device 126a) and writing/transferring the data to the communication circuit 202 to generate a communication signal containing the data to be transmitted to the remote entity 214. It should be appreciated that, transmitting such data stored in the memory 104 to the remote entity 214 can allow for deleting such data from the memory 104 (e.g., via the data communication component 206 deleting such data from a volatile memory component in the memory 104), thereby facilitating improved storage capacity associated with the memory 104 and/or improved processing efficiency associated with the processor 106.

In several embodiments, the data communication component 206 can comprise one or more computer and/or machine readable, writable, and/or executable components and/or instructions that, when executed by the processor 106, can facilitate writing data and/or instructions received, from the remote entity 214, to the data communication component 206 and/or the memory 104. In such embodiments, the data and/or instructions received from the remote entity 214 can comprise instructions directing one or more of the components of the storage component 102 and/or one or more of the device 126a components to execute one or more functions. For example, such instructions can comprise directions to activate, deactivate, execute an operation, modify functionality, and/or the like. In some embodiments, the data communication component 206 can facilitate transmitting to the device 126a (e.g., as described above), the data and/or instructions received from the remote entity 214, for storing, processing, and/or execution by the device 126a.

In other embodiments, the data communication component 206 can comprise one or more computer and/or machine readable, writable, and/or executable components and/or instructions that, when executed by the processor 106, can facilitate communicating to the remote entity 214 over a network, the status of one or more components of the storage component 102 and/or the status of one or more functions executed by one or more components of the storage component 102. For example, the data communication component 206 can facilitate communicating to the remote entity 214, the charging/discharging status of a battery coupled to the charging circuit and power storage 110. In another embodiment, the data communication component 206 can facilitate communicating to the remote entity 214, the status of a sterilization agent and/or a sterilization process employed by the sterilization components 208. In some embodiments, the data communication component 206 can facilitate communicating instructions received from the remote entity 214 to various components of the storage component 102 (e.g., to the processor 106). For example, the data communication component 206 can facilitate communicating instructions received from the remote entity 214 to active/deactivate the sterilization components 208 and/or to employ the charge controller 134 to facilitate execution of one or more functions associated with the charging circuit and power storage 110 (e.g., to charge/discharge a battery coupled to the charging circuit and power storage 110 as described above).

In other embodiments, the data communication component 206 can comprise one or more computer and/or machine readable, writable, and/or executable components and/or instructions that, when executed by the processor 106, can facilitate securing access to the data and/or communication signals transmitted to/received from the remote entity 214 over a network. For instance, the data communication component 206 can facilitate encrypting and/or decrypting the data and/or communication signals transmitted to/received from the remote entity 214 over a network. In other embodiments, the data communication component 206 can facilitate integrating a password protection feature into the communication signal and/or associating a password protection feature with the data. In some embodiments, the data communication component 206 can facilitate integrating a key and value protection feature into the communication signal and/or associating a key and value protection feature with the data. It should be appreciated that implementing such access security components (e.g., via the data communication component 206) can facilitate improved protection of the data communicated between the storage component 102 and the remote entity 214.

In several embodiments, the antenna 210 can comprise a radio frequency antenna (RF antenna). In other embodiments, the antenna 210 can comprise an integrated RF antenna, a patch antenna, a microstrip antenna, a printed antenna, and/or the like, that can facilitate transmitting/receiving the radio waves 212 according to the various embodiments of the subject disclosure described herein.

In numerous embodiments, the one or more remote entity 214 can be any type of component, machine, device, facility, apparatus, and/or instrument that comprises a processor and/or can be capable of effective and/or operative communication with a wired and/or wireless network. All such embodiments are envisioned. For example, the remote entity 214 can be a server device, a computing device, and the like. In various embodiments, components, machines, apparatuses, devices, facilities, and/or instrumentalities that can comprise the remote entity 214 can include tablet computing devices, handheld devices, mobile devices, server class computing machines and/or databases, laptop computers, notebook computers, desktop computers, cell phones, smart phones, consumer appliances and/or instrumentation, industrial and/or commercial devices, digital assistants, multimedia Internet enabled phones, multimedia players, and the like.

According to several embodiments, the storage component 102 can transmit/receive communication signals (e.g., radio waves 212) to/from the remote entity 214, over a network. In numerous embodiments, such a network can include wired and/or wireless networks, including, but not limited to, a cellular network, a wide area network (WAN)

(e.g., the Internet) or a local area network (LAN). For example, the storage component 102 can communicate with the one or more remote entity 214 (and vice versa) using virtually any desired wired or wireless technology, including but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Zigbee and other 802.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, an ANT, an ultra-wideband (UWB) standard protocol, and/or other proprietary and non-proprietary communication protocols. In such an example, the storage component 102 can thus include hardware (e.g., a central processing unit (CPU), a transceiver, a decoder), software (e.g., a set of threads, a set of processes, software in execution) or a combination of hardware and software that facilitates communicating information between the storage component 102 and external systems, sources, and devices.

According to numerous embodiments, the one or more sterilization components 208 can be operatively, electrically, and/or communicatively coupled to the recess 124a and/or an internal or external surface of the recess 124a. In several embodiments, the sterilization components 208 can comprise one or more sterilizing systems, devices, and/or processes that facilitate exposing the device 126a to one or more sterilizing agents (e.g., ultraviolet (UV) radiation/light, thermal radiation, chemical solution, etc.) to sterilize the device 126a. In several embodiments, the memory 104 can comprise one or more computer and/or machine readable, writable, and/or executable components and/or instructions that, when executed by the processor 106, can facilitate the sterilization components 208 (e.g., an ultraviolet (UV) sterilizing system, a thermal radiation/heat source, chemical solution system, etc.) exposing the device 126a to one or more sterilizing agents (e.g., an ultraviolet (UV) LED, heated gas and/or liquid, chemical solution, etc.). For instance, the sterilization components 208 can comprise an ultraviolet (UV) sterilizing system employing, a Light Emitting Diode (LED) light operatively and/or electrically coupled to the recess 124a. In such an example, the ultraviolet (UV) sterilizing system can facilitate (e.g., via the machine-executable instructions executed by the processor 106) exposing the device 126a to ultraviolet light, thereby sterilizing the device 126a. In other embodiments, the sterilization components 208 can comprise a thermal radiation device (e.g., a heat source, heating device, etc.) that exposes the device 126a to heated gas and/or liquid (e.g., air, water, saline solution, etc.). In still other embodiments, the sterilization components 208 can comprise a system for storing and/or injecting one or more chemical solutions into the recess 124a to expose the device 126a to the chemical solution.

It should be appreciated that various embodiments of the subject disclosure described herein can be employed to perform operations that are highly technical in nature, that are not abstract, and that cannot be performed as a set of mental acts by a human. For example, a human could not harvest energy from one or more ambient energy sources, convert the harvested energy to electrical energy, store the electrical energy, and wirelessly transfer the stored electrical energy, by way of inductive coupling, to an electronic device for charging a power source of the electronic device. It should be further appreciated that the storage component 102 and associated components (e.g., the memory 104, the processor 106, the data logging component 204, the data communication component 206, etc.) can automatically process and execute computer and/or machine readable, writable, and/or executable instructions in a manner that cannot be performed by a human (e.g., using techniques, technologies, and/or algorithms that are greater than the capability of a human mind). For example, the quantity of instructions processed, the speed at which the instructions are processed, and/or the variety of different types of instructions processed by the storage component 102 and associated components over a defined period of time can be respectively greater, faster, and differ more than the amount, speed, and variety that can be processed by a human mind over the same period of time.

Figure 3:
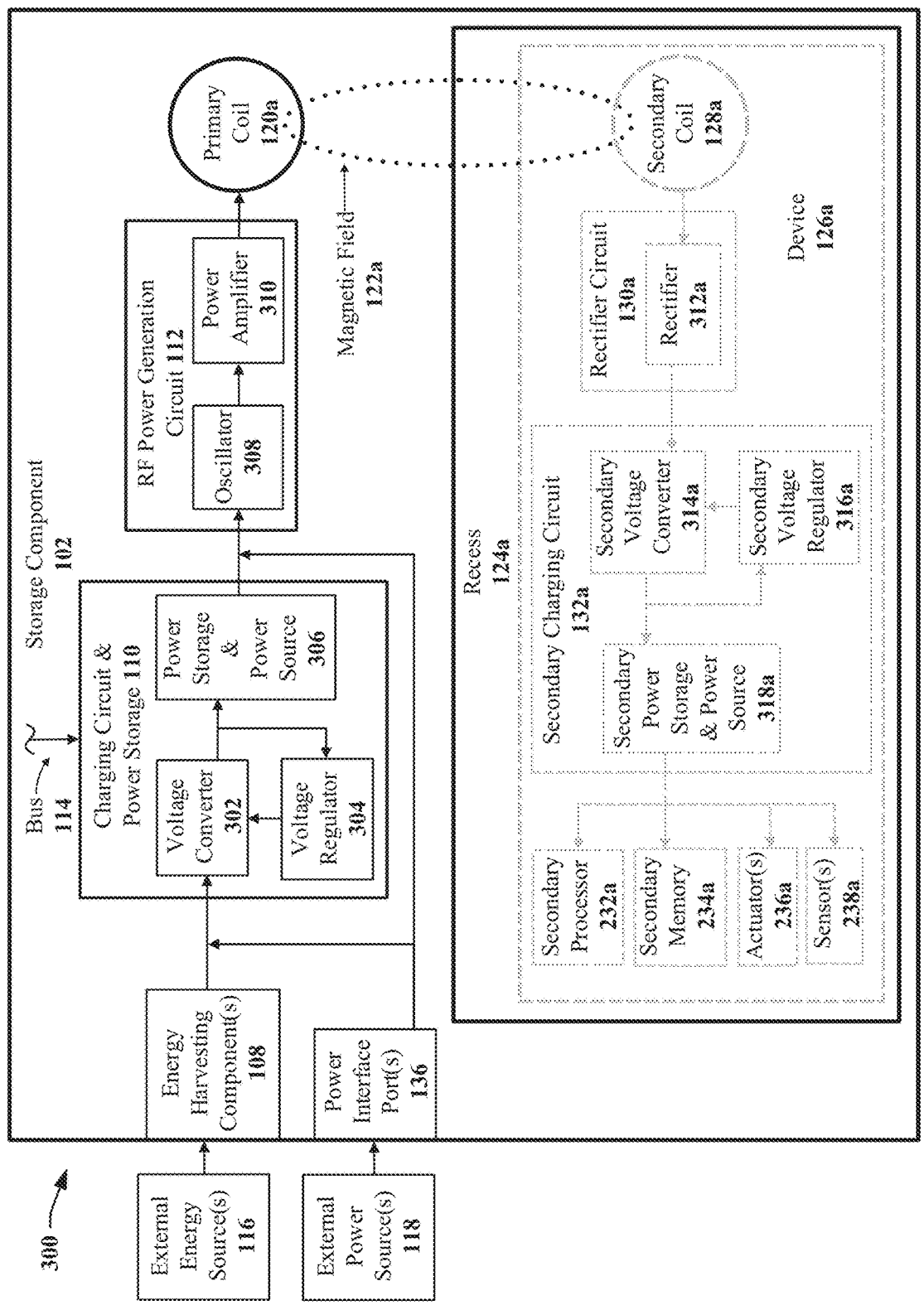
FIG. 3 illustrates a block diagram of another example, non-limiting system 300 that facilitates wirelessly charging one or more electronic devices in accordance with one or more embodiments of the disclosed subject matter.

FIG. 3 illustrates a block diagram of an example, non-limiting system 300 that facilitates wirelessly charging one or more electronic devices in accordance with one or more embodiments of the disclosed subject matter. In one or more embodiments, the system 300 can be a subsystem of the system 100 and/or the system 200 (e.g., the system 100 and/or the system 200 can include the system 300, and vice versa). For purposes of brevity and clarity, FIG. 3 illustrates an embodiment of the storage component 102 comprising a single primary coil 120a, a single magnetic field 122a, and a single recess 124a supporting and/or storing a single device 126a. Although FIG. 3 depicts a single quantity for such components, it should be appreciated that the embodiment shown in FIG. 3 is for illustration only, and as such, the system 300 is not so limited. Repetitive description of like elements employed in respective embodiments is omitted for sake of brevity.

In the embodiment shown in FIG. 3, the system 300 can comprise the storage component 102, the charging circuit and power storage 110, and/or the RF power generation circuit 112. According to several embodiments, the charging circuit and power storage 110 can comprise voltage converter 302, voltage regulator 304, and/or power storage and power source 306. Additionally or alternatively, according to numerous embodiments, the RF power generation circuit 112 can comprise oscillator 308 and/or power amplifier 310. Although the charging circuit and power storage 110, and/or the RF power generation circuit 112 can comprise the components indicated above, it should be appreciated that the embodiment shown in FIG. 3 is for illustration only, and as such, the architecture of the charging circuit and power storage 110, and/or the RF power generation circuit 112 is not so limited. In several embodiments, the voltage converter 302, the voltage regulator 304, the power storage and power source 306, the oscillator 308, the power amplifier 310, and/or the primary coil 120a can be electrically, communicatively, and/or operatively coupled to one another via electrical circuitry.

In some embodiments, the voltage converter 302 can comprise a system, device, and/or electrical circuitry that can facilitate converting voltage (e.g., from lower voltage to higher voltage or vice versa). For example, in some embodiments, the electrical potential associated with the electrical energy transferred by the energy harvesting components 108 can vary (e.g., different voltage values) depending on the type of the energy harvesting components 108 transferring the electrical energy (e.g., solar cell, RF antenna, etc.). In such embodiments, the voltage converter 302 can comprise electrical circuitry that can facilitate converting (e.g., increasing/decreasing) the voltage associated with the direct current transferred from the energy harvesting components 108.

According to multiple embodiments, the voltage regulator 304 can comprise a system, device, and/or electrical circuitry that can facilitate regulating the electrical potential (e.g., the voltage value) of the electrical energy transferred to the power storage and power source 306. In several embodiments, the voltage regulator 304 can operate in conjunction with the voltage converter 302 to facilitate transferring to the power storage and power source 306 electrical energy having a stable, constant, and/or consistent electrical potential (e.g., voltage). In some embodiments, the voltage converter 302 and/or the voltage regulator 304 can operate conjunctively and/or respectively to facilitate providing a minimum voltage value, a maximum voltage value, and/or a discrete voltage value to the power storage and power source 306.

In numerous embodiments, the power storage and power source 306 can comprise a system, device, and/or electrical circuitry that can facilitate storing electrical potential (e.g., voltage and/or current) associated with the electrical energy harvested by the energy harvesting components 108 and/or modified (e.g., as described above) by the voltage converter 302 and/or the voltage regulator 304. For example, the power storage and power source 306 can comprise a battery (e.g., a rechargeable battery) that can accept and store (e.g., initially and/or repeatedly) an electrical charge (e.g., via applying voltage across terminals coupled to the battery). In such an example, the power storage and power source 306 can further discharge (e.g., via terminals and/or electrical circuitry coupled to the battery) the stored electrical charge (e.g., voltage and/or current) to the RF power generation circuit 112. According to multiple embodiments, the power storage and power source 306 can comprise a thin-film solid state battery comprising a voltage capacity ranging between 3.2 V to 4.2 V. In an embodiment, the power storage and power source 306 can comprise a thin-film solid state battery comprising a voltage capacity of 3.7 V.

According to several embodiments, the oscillator 308 can comprise a system, device, and/or electrical circuitry that can facilitate converting a direct electrical current (DC) to an alternating electrical current (AC) and/or signal. For example, the oscillator 308 can comprise a radio frequency (RF) oscillator that can produce signals in the radio frequency range (e.g., about 3 kHz to 300 GHz). In several embodiments, the power amplifier 310 can comprise a system, device, and/or electrical circuitry that can facilitate amplifying (e.g., increasing) the alternating electrical current (AC) and/or signal provided by the oscillator 308. For example, the power amplifier 310 can comprise a radio frequency (RF) amplifier that can amplify signals in the radio frequency range (e.g., about 3 kHz to 300 GHz).

In the embodiment shown in FIG. 3, the system 300 can comprise the recess 124a that receives, supports, and/or stores the device 126a. In numerous embodiments, the device 126a can comprise a rectifier 312a and/or the secondary charging circuit 132a. In other embodiments, the secondary charging circuit 132a can comprise secondary voltage converter 314a, secondary voltage regulator 316a, and/or secondary power storage and power source 318a. Although the device 126a, and/or the secondary charging circuit 132a can comprise the components indicated above, it should be appreciated that the embodiment shown in FIG. 3 is for illustration only, and as such, the architecture of the device 126a, and/or the secondary charging circuit 132a is not so limited. According to multiple embodiments, the secondary coil 128a, the rectifier 312a, the secondary voltage converter 314a, the secondary voltage regulator 316a, and/or the secondary power storage and power source 318a can be electrically, communicatively, and/or operatively coupled to one another via electrical circuitry.

In some embodiments, the rectifier 312a can comprise a system, device, and/or electrical circuitry that can facilitate converting alternating current (AC) to direct current (DC). For example, the rectifier 312a can comprise an electrical circuit that can facilitate converting the alternating current induced in the secondary coil 128a (e.g., as described above with reference to FIG. 1) to a direct current. In several embodiments, the rectifier 312a can further facilitate transferring (e.g., via electrical circuitry) the direct current to the secondary charging circuit 132a, the secondary voltage converter 314a, the secondary voltage regulator 316a, and/or the secondary power storage and power source 318a.

According to several embodiments, the secondary voltage converter 314a can comprise a system, device, and/or electrical circuitry (e.g., as described above) that can facilitate converting voltage (e.g., from lower voltage to higher voltage or vice versa). For example, the secondary voltage converter 314a can comprise electrical circuitry that can facilitate converting (e.g., increasing/decreasing) voltage associated with the direct current transferred from the rectifier 312a.

According to multiple embodiments, the secondary voltage regulator 316a can comprise a system, device, and/or electrical circuitry that can facilitate regulating the electrical potential (e.g., the voltage value) of the electrical energy transferred to the secondary power storage and power source 318a. In several embodiments, the secondary voltage regulator 316a can operate in conjunction with the secondary voltage converter 314a to facilitate transferring to the secondary power storage and power source 318a electrical energy having a stable, constant, and/or consistent electrical potential (e.g., voltage). In some embodiments, the secondary voltage converter 314a and/or the secondary voltage regulator 316a can operate conjunctively and/or respectively to facilitate providing a minimum voltage value, a maximum voltage value, and/or a discrete voltage value to the secondary power storage and power source 318a.

In numerous embodiments, the secondary power storage and power source 318a can comprise a system, device, and/or electrical circuitry that can facilitate storing electrical potential (e.g., voltage and/or current) associated with the electrical energy modified (e.g., as described above) by the secondary voltage converter 314a and/or the secondary voltage regulator 316a. For example, the secondary power storage and power source 318a can comprise a battery (e.g., a rechargeable battery) that can accept and store (e.g., initially and/or repeatedly) an electrical charge (e.g., via applying voltage across terminals coupled to the battery). In this example, accepting and storing the electrical charge by the secondary power storage and power source 318a is indicative of charging the secondary power storage and power source 318a. In such an example, the secondary power storage and power source 318a can further discharge (e.g., via terminals and/or electrical circuitry coupled to the battery) the stored electrical charge (e.g., voltage and/or current) to one or more components of the device 126a (e.g., the secondary processor 232a, the secondary memory 234a, the actuators 236, and/or the sensors 238a). According to multiple embodiments, the secondary power storage and power source 318a can comprise a thin-film solid state battery comprising a voltage capacity ranging between 3.2 V to 4.2 V. In an embodiment, the secondary power storage and power source 318a can comprise a thin-film solid state battery comprising a voltage capacity of 3.7 V.

Figure 4:
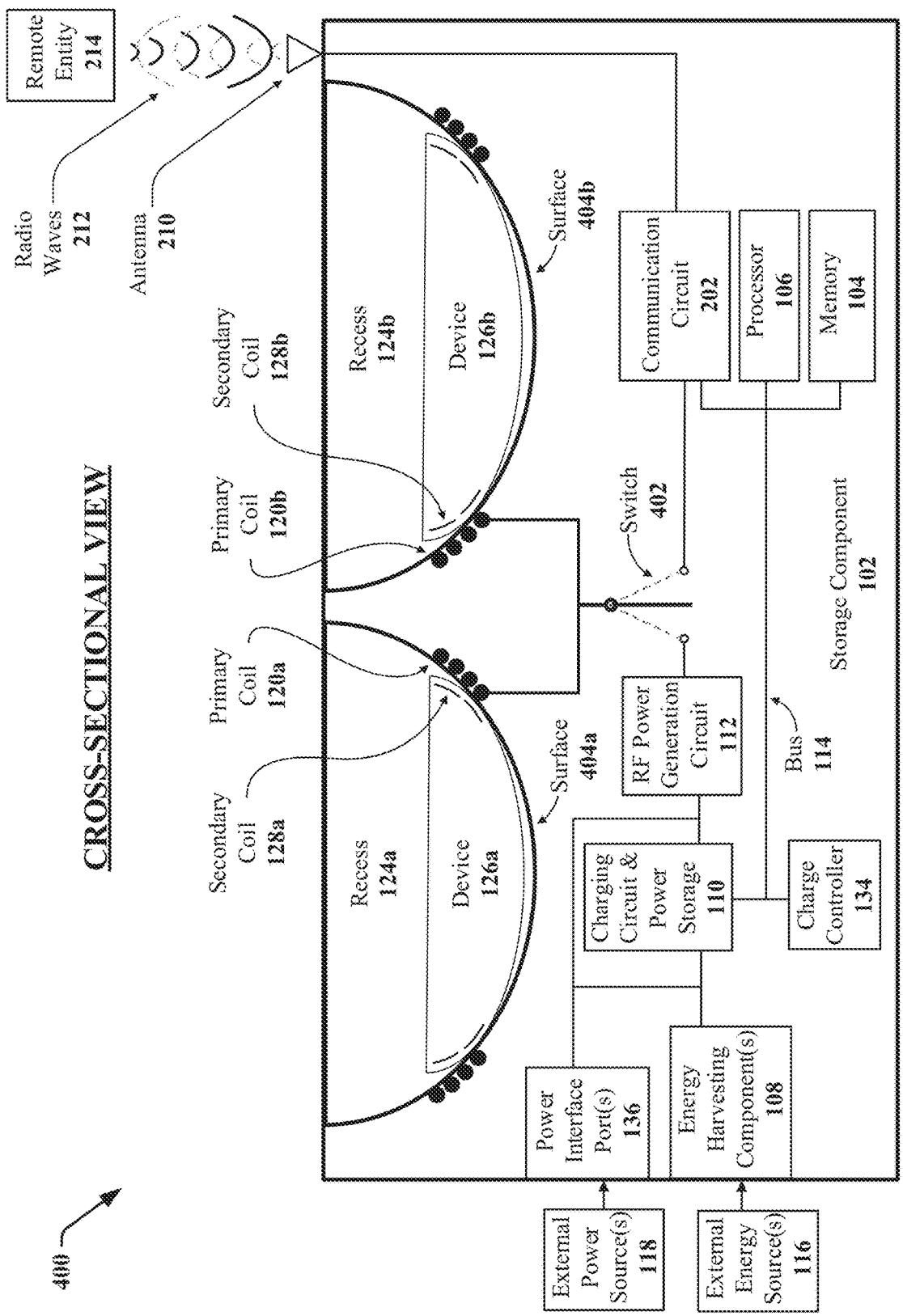
FIG. 4 illustrates a block diagram of another example, non-limiting system 400 that facilitates wirelessly charging and/or communicating with one or more electronic devices in accordance with one or more embodiments of the disclosed subject matter.

FIG. 4 illustrates a block diagram of an example, non-limiting system 400 that facilitates wirelessly charging and/or communicating with one or more electronic devices in accordance with one or more embodiments of the disclosed subject matter. In one or more embodiments, the system 400 can be a subsystem of the system 100, the system 200, and/or the system 300 (e.g., the system 100, the system 200, and/or the system 300 can include the system 400, and vice versa). Repetitive description of like elements employed in respective embodiments is omitted for sake of brevity. In the embodiment shown in FIG. 4, the system 400 can comprise the storage component 102 comprising switch 402, and/or one or more surface 404a, 404b of the recess 124a, 124b.

According to multiple embodiments, the switch 402 can comprise any one of a variety of switches (e.g., analog, digital, electronic, mechanical, etc.) that can facilitate switching between an electrical circuit coupling the RF power generation circuit 112 with the primary coil 120a, 120b and an electrical circuit coupling the communication circuit 202 with the primary coil 120a, 120b. In several embodiments, the switch 402 can comprise an electronic switch (e.g., a solid state switch, bipolar transistor, power diode, etc.). In many embodiments, the switch 402 can be coupled (e.g., electrically, operatively, communicatively, etc.) to the charging circuit and power storage 110 (e.g., the power storage and power source 306), the RF power generation circuit 112, the bus 114, the primary coil 120a, 120b, the communication circuit 202, and/or a microcontroller (not illustrated in FIG. 4). In such embodiments, the microcontroller can comprise a memory that can store computer and/or machine readable, writable, and/or executable components and/or instructions that, when executed by the microcontroller, can facilitate the microcontroller actuating the switch 402 (e.g., digitally and/or electronically). In other embodiments, the memory 104 can store computer and/or machine readable, writable, and/or executable components and/or instructions that, when executed by the processor 106, can facilitate actuation of the switch 402 (e.g., an electronic switch). In still other embodiments, the switch 402 can comprise a mechanical switch (e.g., push button, toggle, single pole double throw, etc.) that can be coupled (e.g., electrically, operatively, communicatively, etc.) to the storage component 102, the RF power generation circuit 112, the bus 114, the primary coil 120a, 120b, and/or the communication circuit 202. In such embodiments, the switch 402 can be activated and/or engaged by a user and/or entity to facilitate mechanical actuation of the switch 402.

As illustrated by the embodiment depicted in FIG. 4, the inductive coupling and/or the wireless data transmission operations described herein with reference to the system 100 and/or the system 200, as well as FIG. 1 and/or FIG. 2, can be facilitated utilizing the primary coil 120a, 120b for all such operations (e.g., as opposed to utilizing the primary coil 120a, 120b for inductively coupling operations and utilizing the primary communication antenna 220a for wireless data transmission operations). According to several embodiments, the switch 402 can facilitate coupling (e.g., via electronic and/or mechanical actuation as described above) the RF power generation circuit 112 with the primary coil 120a, 120b to inductively couple the primary coil 120a, 120b to the secondary coil 128a, 128b, thereby facilitating inductively charging a power source of the device 126a, 126b as described above. In other embodiments, the switch 402 can couple (e.g., via electronic and/or mechanical actuation as described above) the communication circuit 202 with the primary coil 120a, 120b to facilitate wireless transmission of data to, and/or receipt of data from, the device 126a, 126b (e.g., the secondary communication circuit 230a) as described above.

In some embodiments, the storage component 102 and/or the recess 124a, 124b can comprise one or more surfaces, guiding structures, and/or support structures that can receive, guide, and/or support the device 126a, 126b in such a manner to facilitate optimal alignment (e.g., planar, axial, proximal, etc.) of the primary coil 120a, 120b with the secondary coil 128a, 128b. For example, the recess 124a, 124b can comprise one or more surface 404a, 404b that can be configured (e.g., as a concaved surface) to receive and/or support a corresponding surface (e.g., a convex surface) of the device 126a, 126b. In such an example, the primary coil 120a, 120b and/or the secondary coil 128a, 128b can respectively comprise a multi-turn inductive coil antenna. In this example, the primary coil 120a, 120b can be integrated in the surface 404a, 404b and/or wrapped or coiled around the perimeter of the recess 124a, 124b. Continuing with this example, the primary coil 120a, 120b can comprise an inner diameter that is larger than the outer diameter of the device 126a, 126b, thereby facilitating locating the secondary coil 128a, 128b inside and immediately adjacent to the primary coil 120a, 120b. In such an example, locating the secondary coil 128a, 128b inside and immediately adjacent to the primary coil 120a, 120b can facilitate optimal alignment (e.g., planar, axial, proximal, etc.) of the primary coil 120a, 120b with the secondary coil 128a, 128b. According to multiple embodiments, the primary coil 120a, 120b can be integrated in the surface 404a, 404b and/or wrapped or coiled around the perimeter of the recess 124a, 124b during fabrication and/or manufacturing by employing the same or similar fabrication and/or manufacturing techniques and/or materials described above with reference to FIG. 1 (e.g., via printing techniques/materials, semiconductor lithography techniques/materials, and/or the like).

Figure 5:
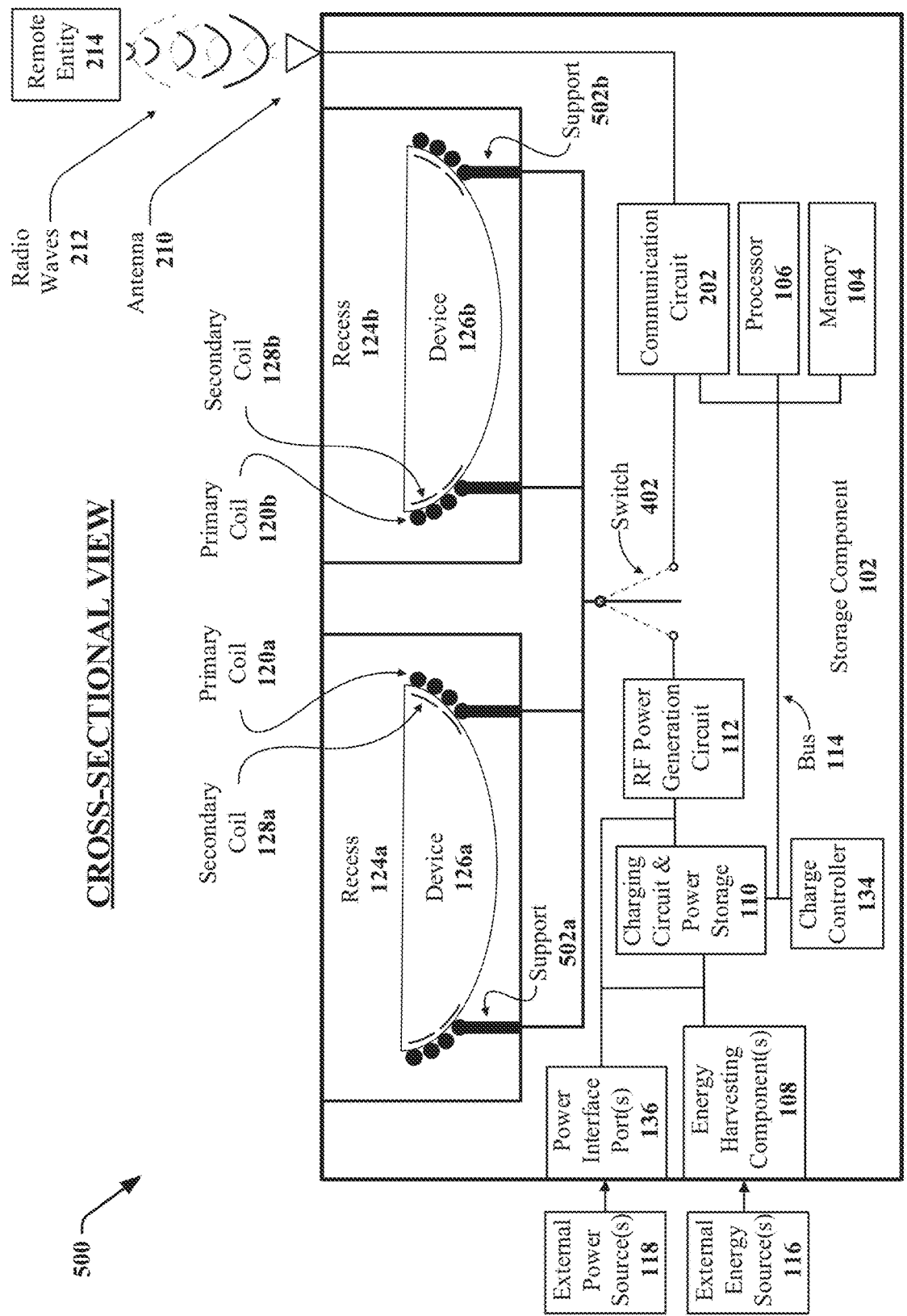
FIG. 5 illustrates a block diagram of another example, non-limiting system 500 that facilitates wirelessly charging and/or communicating with one or more electronic devices in accordance with one or more embodiments of the disclosed subject matter.

FIG. 5 illustrates a block diagram of an example, non-limiting system 500 that facilitates wirelessly charging and/or communicating with one or more electronic devices in accordance with one or more embodiments of the disclosed subject matter. In one or more embodiments, the system 500 can be a subsystem of the system 100, the system 200, the system 300, and/or the system 400 (e.g., the system 100, the system 200, the system 300, and/or the system 400 can include the system 500, and vice versa). Repetitive description of like elements employed in respective embodiments is omitted for sake of brevity. In the embodiment shown in FIG. 5, the system 500 can comprise the storage component 102 comprising one or more support 502a, 502 located in the recess 124a, 124b.

In some embodiments, the storage component 102 and/or the recess 124a, 124b can comprise one or more surfaces, guiding structures, and/or support structures that can receive, guide, and/or support the device 126a, 126b in such a manner to facilitate optimal alignment (e.g., planar, axial, proximal, etc.) of the primary coil 120a, 120b with the secondary coil 128a, 128b. For example, the recess 124a, 124b can comprise one or more support 502a, 502b that can be configured (e.g., as a cylinder, as one or more posts, etc.) to receive and/or support a corresponding surface (e.g., a convex surface, a flat surface, etc.) of the device 126a, 126b. In such an example, the primary coil 120a, 120b and/or the secondary coil 128a, 128b can respectively comprise a multi-turn inductive coil antenna. In this example, the primary coil 120a, 120b can be integrated in and/or extend from the support 502a, 502b (e.g., as depicted in FIG. 5) such that the multi-turn inductive coils of the primary coil 120a, 120b wrap or coil around a periphery and/or perimeter surface of the device 126a, 126b (e.g., as depicted in FIG. 5). Continuing with this example, the primary coil 120a, 120b can comprise an inner diameter that is larger than the outer diameter of the device 126a, 126b, thereby facilitating locating the secondary coil 128a, 128b inside and immediately adjacent to the primary coil 120a, 120b. In such an example, locating the secondary coil 128a, 128b inside and immediately adjacent to the primary coil 120a, 120b can facilitate optimal alignment (e.g., planar, axial, proximal, etc.) of the primary coil 120a, 120b with the secondary coil 128a, 128b. According to multiple embodiments, the primary coil 120a, 120b can be integrated in, and/or structured to extend from, the support 502a, 502b during fabrication and/or manufacturing by employing the same or similar fabrication and/or manufacturing techniques and/or materials described above with reference to FIG. 1 (e.g., via printing techniques/materials, semiconductor lithography techniques/materials, and/or the like).

Figure 6:
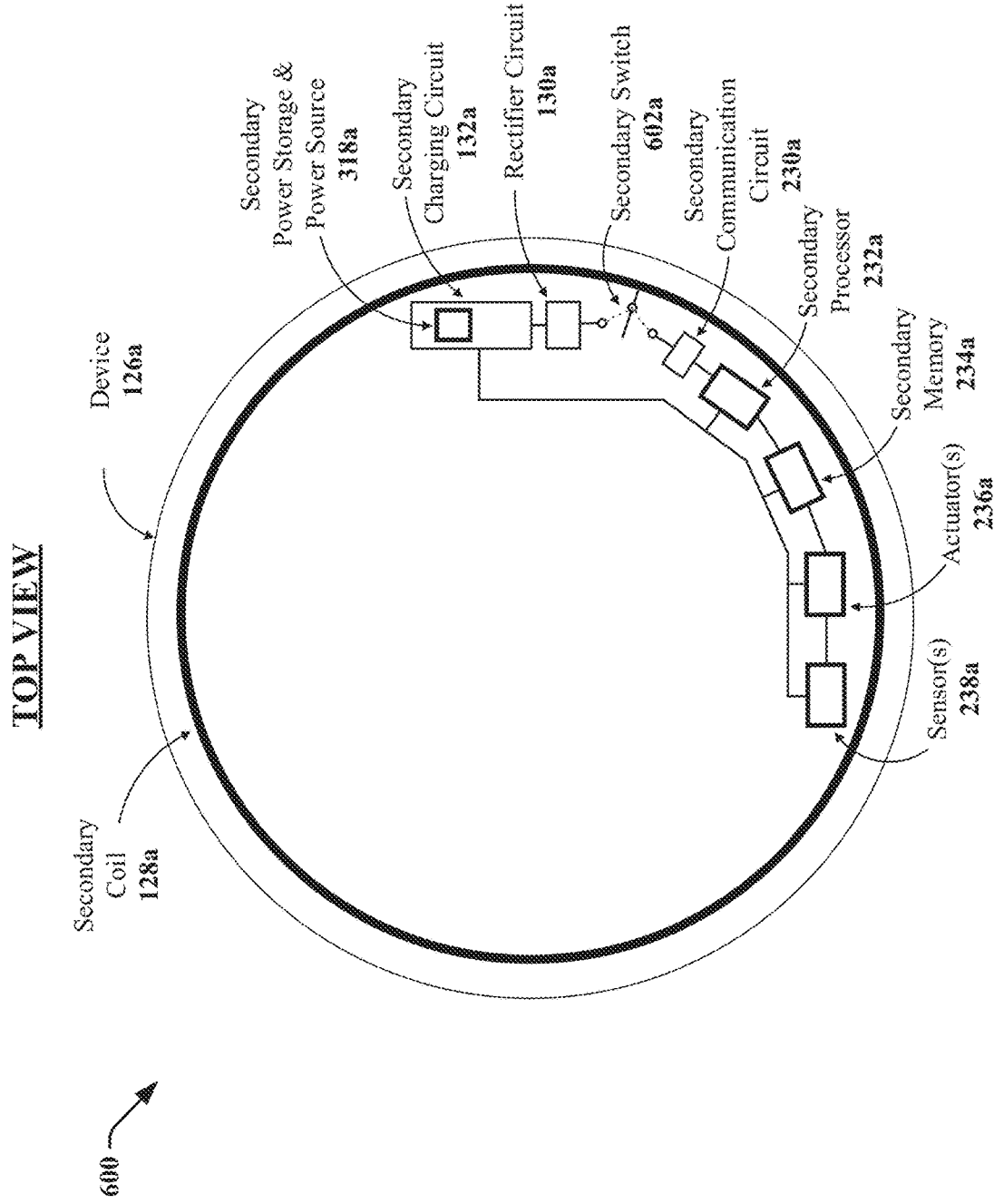
FIG. 6 illustrates a block diagram of another example, non-limiting system 600 that facilitates wirelessly charging and/or communicating with one or more electronic devices in accordance with one or more embodiments of the disclosed subject matter.

FIG. 6 illustrates a block diagram of an example, non-limiting system 600 that facilitates wirelessly charging and/or communicating with one or more electronic devices in accordance with one or more embodiments of the disclosed subject matter. In one or more embodiments, the system 600 can be a subsystem of the system 100, the system 200, the system 300, the system 400, and/or the system 500 (e.g., the system 100, the system 200, the system 300, the system 400, and/or the system 500 can include the system 600, and vice versa). Repetitive description of like elements employed in respective embodiments is omitted for sake of brevity. In the embodiment shown in FIG. 6, the system 600 can comprise the device 126a (e.g., a contact lens), the secondary coil 128a, the rectifier circuit 130a, the secondary charging circuit 132a, the secondary communication circuit 230a, the secondary processor 232a, the secondary memory 234a, the actuators 236a, the sensors 238a, the secondary power storage and power source 318a, and/or the secondary switch 602a.

According to multiple embodiments, the secondary switch 602a can comprise any one of a variety of switches (e.g., analog, digital, electronic, mechanical, etc.) that can facilitate switching between an electrical circuit coupling the rectifier circuit 130a with the secondary coil 128a and an electrical circuit coupling the secondary communication circuit 230a with the secondary coil 128a. In several embodiments, the secondary switch 602a can comprise an electronic switch (e.g., a solid state switch, bipolar transistor, power diode, etc.). In many embodiments, the secondary switch 602a can be coupled (e.g., electrically, operatively, communicatively, etc.) to the rectifier circuit 130a, the secondary charging circuit 132a (e.g., the secondary power storage and power source 318a), the secondary coil 128a, the secondary communication circuit 230a, and/or a microcontroller (not illustrated in FIG. 6). In such embodiments, the microcontroller can comprise a memory that can store computer and/or machine readable, writable, and/or executable components and/or instructions that, when executed by the microcontroller, can facilitate the microcontroller actuating the secondary switch 602a (e.g., digitally and/or electronically). In other embodiments, the secondary memory 234a can store computer and/or machine readable, writable, and/or executable components and/or instructions that, when executed by the secondary processor 232a, can facilitate actuation of the secondary switch 602a (e.g., an electronic switch). In still other embodiments, the secondary switch 602a can comprise a mechanical switch (e.g., push button, toggle, single pole double throw, etc.) that can be coupled (e.g., electrically, operatively, communicatively, etc.) to the device 126a, the rectifier circuit 130a, the secondary coil 128a, and/or the secondary communication circuit 230a. In such embodiments, the secondary switch 602a can be activated and/or engaged by a user and/or entity to facilitate mechanical actuation of the secondary switch 602a.

As illustrated by the embodiment depicted in FIG. 6, the inductive coupling and/or the wireless data transmission operations described herein with reference to the system 100 and/or the system 200, as well as FIG. 1 and/or FIG. 2, can be facilitated utilizing the secondary coil 128a for all such operations (e.g., as opposed to utilizing the secondary coil 128a for inductively coupling operations and utilizing the secondary communication antenna 228a for wireless data transmission operations). According to several embodiments, the secondary switch 602a can facilitate coupling (e.g., via electronic and/or mechanical actuation as described above) the rectifier circuit 130a with the secondary coil 128a to inductively couple the secondary coil 128a to the primary coil 120a, thereby facilitating inductively charging the secondary power storage and power source 318a of the device 126a as previously described. In other embodiments, the secondary switch 602a can couple (e.g., via electronic and/or mechanical actuation as described above) the secondary communication circuit 230a with the secondary coil 128a to facilitate wireless transmission of data to, and/or receipt of data from, the storage component 102 (e.g., the communication circuit 202) as previously described.

Figure 7:
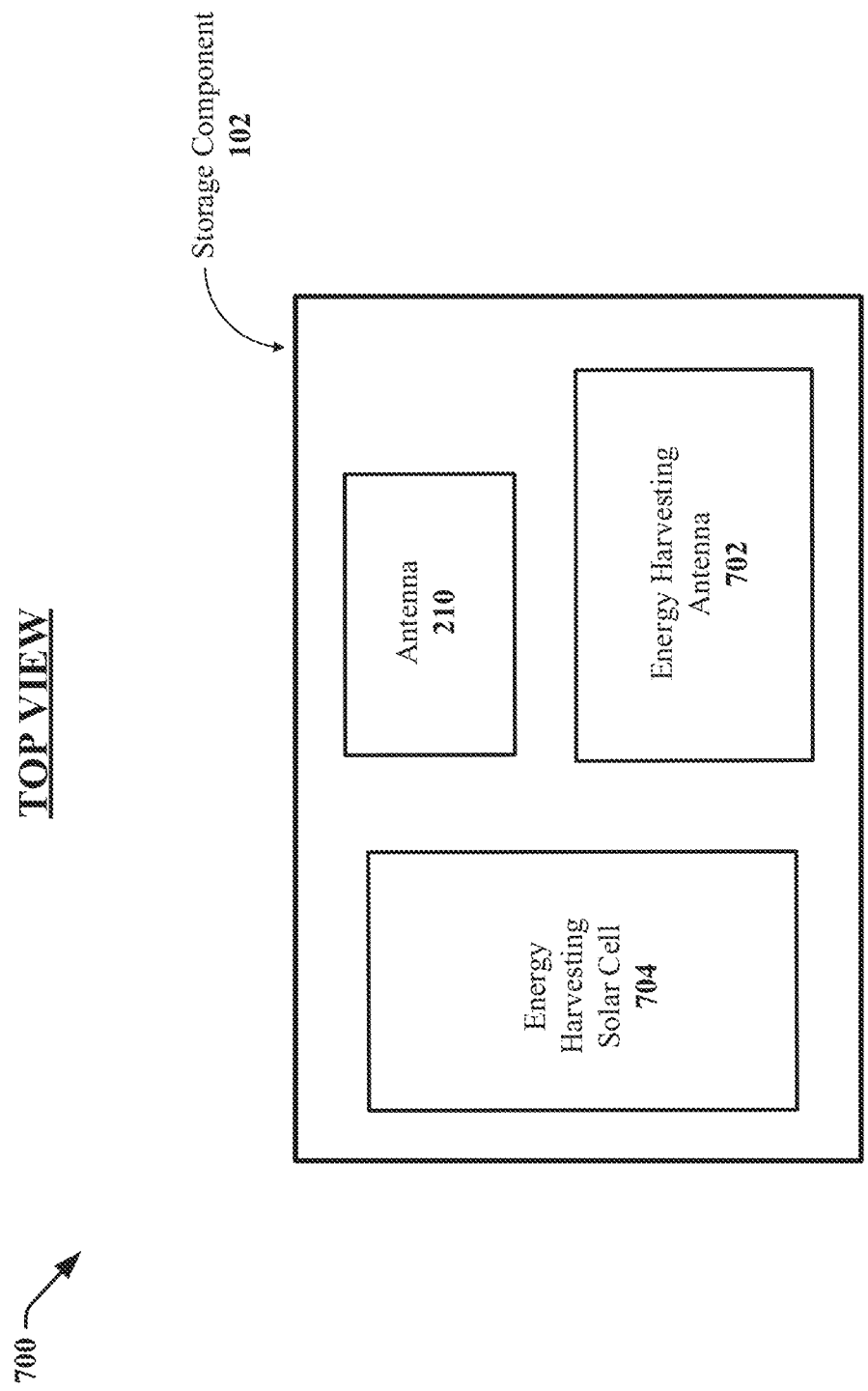
FIG. 7 illustrates a block diagram of another example, non-limiting system 700 that facilitates wirelessly charging and/or communicating with one or more electronic devices in accordance with one or more embodiments of the disclosed subject matter.

FIG. 7 illustrates a block diagram of an example, non-limiting system 700 that facilitates wirelessly charging and/or communicating with one or more electronic devices in accordance with one or more embodiments of the disclosed subject matter. In one or more embodiments, the system 700 can be a subsystem of the system 100, the system 200, the system 300, the system 400, the system 500, and/or the system 600 (e.g., the system 100, the system 200, the system 300, the system 400, the system 500, and/or the system 600 can include the system 700, and vice versa). Repetitive description of like elements employed in respective embodiments is omitted for sake of brevity. In the embodiment shown in FIG. 7, the system 700 can comprise the storage component 102, the antenna 210, the energy harvesting antenna 702, and/or the energy harvesting solar cell 704.

According to multiple embodiments, the energy harvesting antenna 702 can comprise one or more radio frequency receiver antennae that can intercept ambient radio waves propagating through the atmosphere to capture electromagnetic radiant energy (e.g., as described above with reference to the energy harvesting components 108 and FIG. 1). For instance, the oscillating transverse magnetic and electric fields inherent to the radio waves can apply oscillating forces on the electrons in the atoms of the material of the energy harvesting antenna 702, thereby producing an alternating electric current in the energy harvesting antenna 702. In such an example, the energy harvesting antenna 702 can comprise terminals that can be electrically coupled (e.g., via electrical circuitry) to a rectifier that can convert the alternating electric current to direct electric current. In several embodiments, the energy harvesting antenna 702, and/or the rectifier electrically coupled thereto, can facilitate transferring the electrical energy (e.g., the direct electric current) to the charging circuit and power storage 110 (e.g., via the bus 114 and/or electrical circuitry as described above with reference to the charging circuit and power storage 110 and FIG. 1).

In some embodiments, the energy harvesting solar cell 704 can comprise one or more photovoltaic cells (e.g., solar cells) that can absorb light (e.g., sunlight and/or artificial light, such as light produced by a Light-Emitting Diode (LED), etc.) and convert the energy in the light to electrical energy (e.g., via the photovoltaic effect). For example, the light energy absorbed by the energy harvesting solar cell 704 can excite electrons in the material of the energy harvesting solar cell 704 to a higher-energy state, thereby creating an electric potential (e.g., a voltage) in atoms of the material of the energy harvesting solar cell 704, which the energy harvesting solar cell 704 can convert to a direct electrical current. In several embodiments, the energy harvesting solar cell 704 can facilitate transferring the electrical energy (e.g., the direct electric current) to the charging circuit and power storage 110 (e.g., via the bus 114 and/or electrical circuitry as described above with reference to the charging circuit and power storage 110 and FIG. 1).

In some embodiments, one or more of the antenna 210, the energy harvesting antenna 702, and/or the energy harvesting solar cell 704 can be integrated in and/or positioned on one or more surfaces of the storage component 102 (e.g., an external top surface, as depicted in the embodiment illustrated in FIG. 7). According to multiple embodiments, the antenna 210, the energy harvesting antenna 702, and/or the energy harvesting solar cell 704 can be integrated in and/or positioned on one or more surfaces of the storage component 102 during fabrication and/or manufacturing by employing the same or similar fabrication and/or manufacturing techniques and/or materials described above with reference to FIG. 1 (e.g., via printing techniques/materials, semiconductor lithography techniques/materials, and/or the like).

Figure 8:
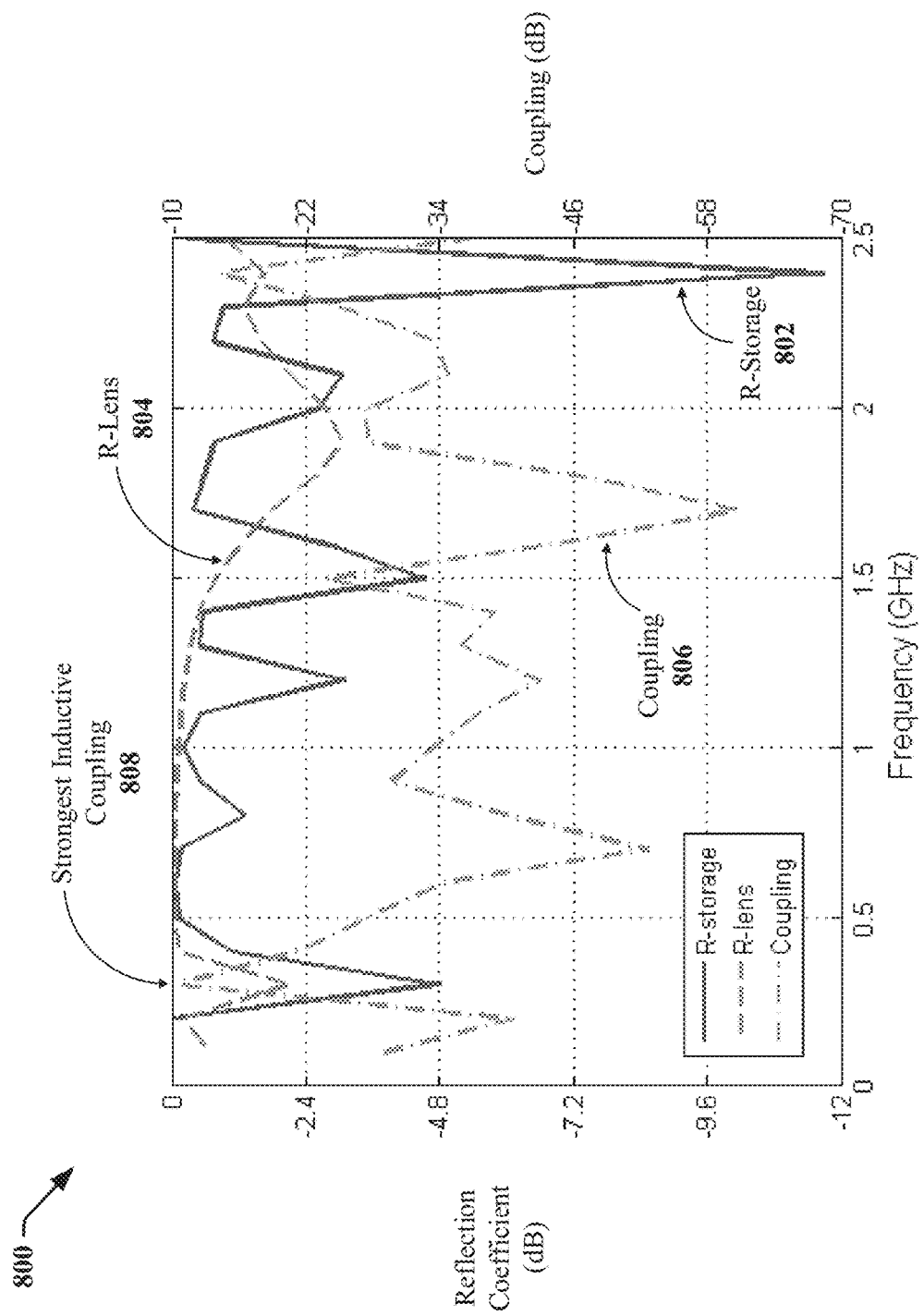
FIG. 8 illustrates non-limiting example information 800 of electromagnetic simulated inductive coupling in accordance with one or more embodiments of the disclosed subject matter.

FIG. 8 illustrates non-limiting example information 800 of electromagnetic simulated inductive coupling in accordance with one or more embodiments of the disclosed subject matter. In various embodiments, information 800 depicted in FIG. 8 can include or be included within one or more of the components and/or functionality of the system 100, the system 200, the system 300, the system 400, the system 500, the system 600, the system 700, and vice versa. Repetitive description of like elements employed in other embodiments described herein is omitted for sake of brevity.

According to some embodiments, the information 800 can comprise information and/or results of an electromagnetic simulated inductive coupling through saline solution in accordance with one or more embodiments of the disclosed subject matter. In several embodiments, the information 800 can comprise R-storage 802, R-lens 804, coupling 806, and/or strongest inductive coupling 808.

In numerous embodiments, R-Storage 802 can comprise the reflection coefficient (e.g., measured in decibels (dB)) corresponding to the storage component 102, the primary coil 120a, 120b, and/or the recess 124a, 124b. In other embodiments, the R-lens 804 can comprise the reflection coefficient (e.g., measured in decibels (dB)) corresponding to the device 126a, 126b and/or the secondary coil 128a, 128b. In still other embodiments, the coupling 806 can comprise the coupling values (e.g., attenuation values measured in decibels (dB)) corresponding to inductive coupling, through a saline solution, of the primary coil 120a, 120b to the secondary coil 128a, 128b. In several embodiments, the strongest inductive coupling 808 can comprise the coupling value (e.g., attenuation value measured in decibels (dB)) corresponding to the electromagnetic signal frequency value (e.g. measured in Hertz (GHz)) that results in the strongest inductive coupling, through a saline solution, between the primary coil 120a, 120b and the secondary coil 128a, 128b. According to an embodiment, as illustrated in the information 800 depicted in FIG. 8, the strongest inductive coupling 808 corresponds to a coupling value of −10.5 dB and an electromagnetic signal frequency value of 300 MHz.

Figure 9:
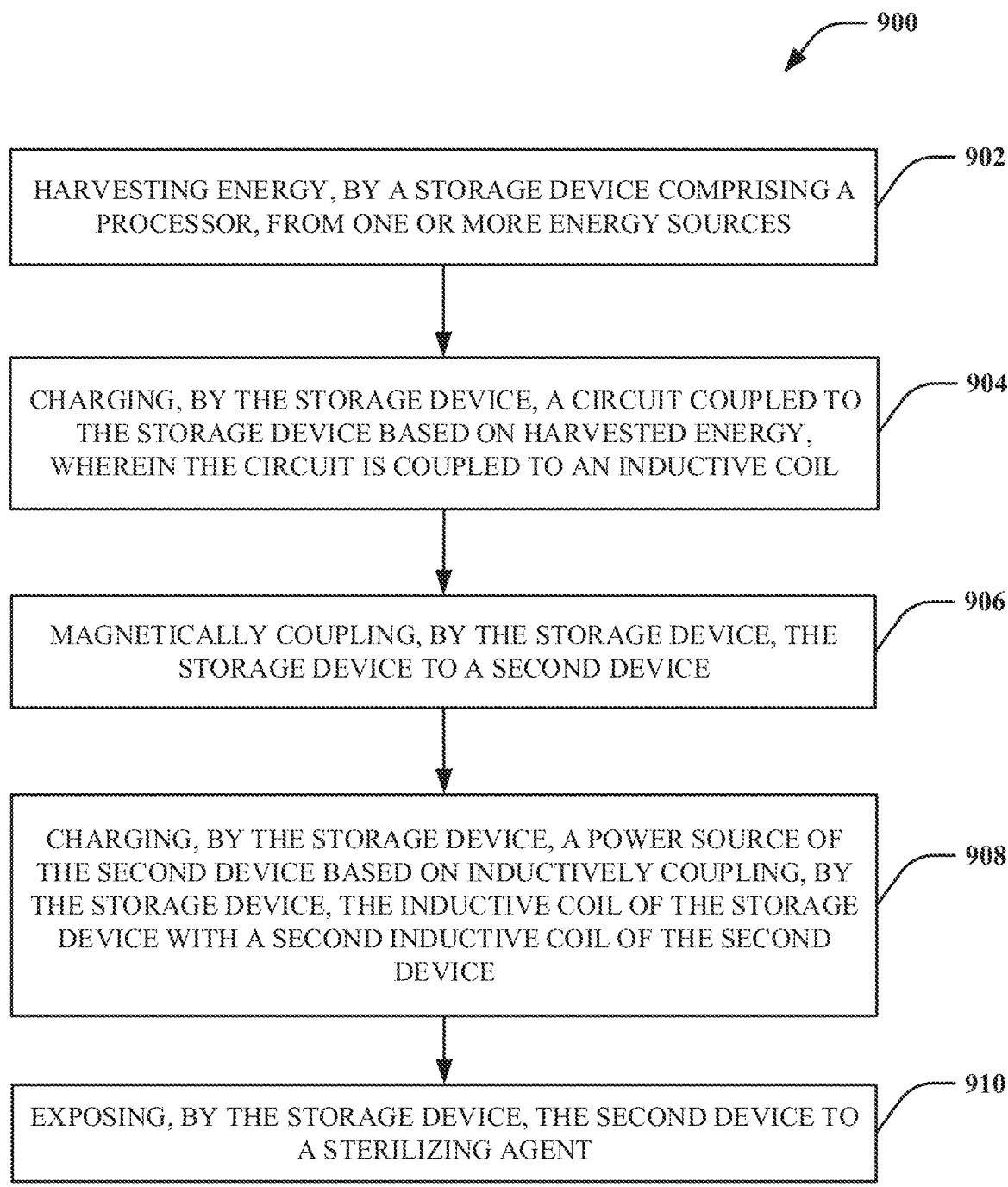
FIG. 9 illustrates a flow diagram of an example, non-limiting computer-implemented process 900 that facilitates wirelessly charging one or more electronic devices in accordance with one or more embodiments of the disclosed subject matter

FIG. 9 illustrates a flow diagram of an example, non-limiting computer-implemented process 900 that facilitates wirelessly charging one or more electronic devices in accordance with one or more embodiments of the disclosed subject matter. Repetitive description of like elements employed in other embodiments described herein is omitted for sake of brevity.

At 902, a storage device (e.g., the storage component 102) comprising and/or operatively coupled to a processor (e.g., the processor 106), can harvest energy (e.g., via the energy harvesting components 108) from one or more energy sources (e.g., electromagnetic radiant energy, solar energy, ultrasonic energy, thermal energy, kinetic energy, wind energy, light energy, ambient energy, and/or the like). In an embodiment, the storage device (e.g., via the energy harvesting antenna 702) can harvest electromagnetic radiant energy from ambient radio waves propagating through the atmosphere (e.g., according to Faraday's law of induction) and convert the electromagnetic radiant energy to electrical energy, such as a direct current (e.g., via a rectifier). In another embodiment, the storage device (e.g., via the energy harvesting solar cell 704) can harvest energy from sunlight and/or artificial light and covert (e.g., via the photovoltaic effect) the light energy to electrical energy, such as a direct current.

At 904, the storage device (e.g., the storage component 102) can charge (e.g., via the energy harvesting components 108) a circuit coupled to the storage device (e.g., the charging circuit and power storage 110 and/or the RF power generation circuit 112) based on harvested energy (e.g., via the energy harvesting components 108). The circuit (e.g., the charging circuit and power storage 110 and/or the RF power generation circuit 112) can be coupled to an inductive coil (e.g., the primary coil 120a, 120b).

At 906, the storage device (e.g., the storage component 102) can magnetically couple (e.g., via one or more magnetic components) the storage device to a second device (e.g., the device 126a, 126b). According to an embodiment, the storage device (e.g., the storage component 102) and/or the second device (e.g., the device 126a, 126b) can comprise one or more magnetic components (e.g., magnets, magnetic coating, magnetic paint, ferromagnetic material, etc.) that can magnetically couple the storage device (e.g., the storage component 102) to the second device (e.g., the device 126a, 126b).

At 908, the storage device (e.g., the storage component 102) can charge a power source (e.g., the secondary power storage and power source 318a) of the second device (e.g., the device 126a, 126b) based on inductively coupling, by the storage device, the inductive coil of the storage device (e.g., the primary coil 120a, 120b of the storage component 102) with a second inductive coil of the second device (e.g., the secondary coil 128a, 128b of the device 126a, 126b). At 910, the storage device (e.g., the storage component 102 and/or the sterilization components 208) can expose the second device (e.g., the device 126a, 126b) to a sterilizing agent (e.g., ultraviolet (UV) radiation/light, thermal radiation, chemical solution, etc.).

Figure 10:
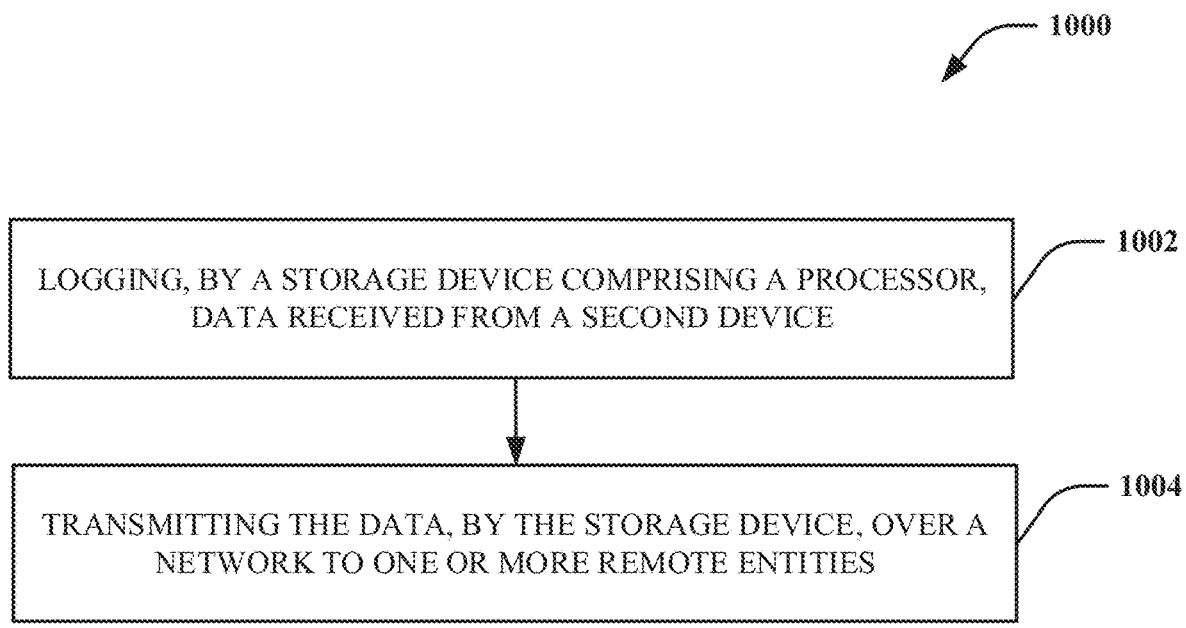
FIG. 10 illustrates a flow diagram of an example, non-limiting computer-implemented process 1000 that facilitates wirelessly communicating with one or more electronic devices in accordance with one or more embodiments of the disclosed subject matter.

FIG. 10 illustrates a flow diagram of an example, non-limiting computer-implemented process 1000 that facilitates wirelessly communicating with one or more electronic devices in accordance with one or more embodiments of the disclosed subject matter. Repetitive description of like elements employed in other embodiments described herein is omitted for sake of brevity.

At 1002, a storage device (e.g., the storage component 102) comprising and/or operatively coupled to a processor (e.g., the processor 106), can log data (e.g., via the data logging component 204 and/or the data communication component 206) received (e.g., via the primary communication antenna 220a and/or the communication circuit 202) from a second device (e.g., the device 126a, 126b). At 1004, the storage device (e.g., the storage component 102) can transmit the data (e.g., via the communication circuit 202 and/or the antenna 210) over a network (e.g., the Internet) to one or more remote entities (e.g., the remote entity 214). In an embodiment, the storage device (e.g., the storage component 102) can transmit the data (e.g., via the communication circuit 202 and/or the antenna 210) over a network (e.g., the Internet) to one or more remote entities (e.g., the remote entity 214). In another embodiment, the storage device (e.g., the storage component 102) can receive data (e.g., via the communication circuit 202 and/or the antenna 210) over a network (e.g., the Internet) from one or more remote entities (e.g., the remote entity 214). In still another embodiment, the storage device (e.g., the storage component 102) can transmit the data (e.g., via the communication circuit 202 and/or the primary communication antenna 220a) to the second device (e.g., the device 126a, 126b).

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed herein are capable of being stored on an article of manufacture to facilitate transporting and transferring such computer-implemented methodologies to computers. The term article of manufacture, as used herein, is intended to encompass a computer program accessible from any computer-readable device or storage media.

Figure 11:
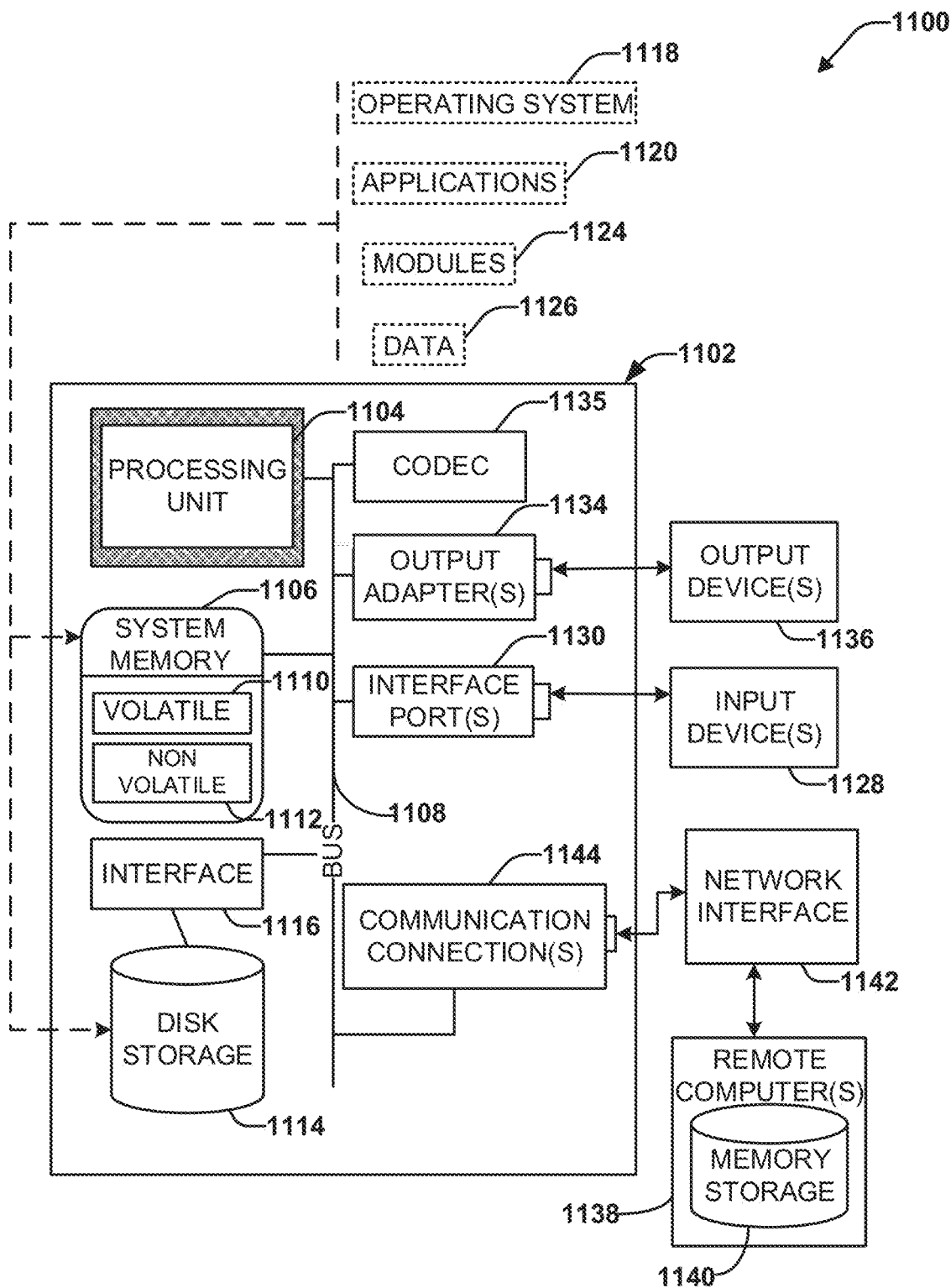
FIG. 11 illustrates a block diagram of an example, non-limiting operating environment 1100 in which one or more embodiments described herein can be facilitated.

FIG. 11 illustrates a block diagram of an example, non-limiting operating environment 1100 in which one or more embodiments described herein can be facilitated. Repetitive description of like elements employed in other embodiments described herein is omitted for sake of brevity. In order to provide a context for the various aspects of the disclosed subject matter, FIG. 11 as well as the following discussion are intended to provide a general description of a suitable operating environment in which the various aspects of the disclosed subject matter can be implemented.

With reference to FIG. 11, an example of the operating environment 1100 for implementing various aspects of the claimed subject matter can include a computer 1102. The computer 1102 can include a processing unit 1104, a system memory 1106, a codec 1135, and a system bus 1108. The system bus 1108 can couple system components including, but not limited to, the system memory 1106 to the processing unit 1104. The processing unit 1104 can be any of various available processors. Dual microprocessors and other multiprocessor architectures also can be employed as the processing unit 1104.

The system bus 1108 can be any of several types of bus structure(s) including a memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1106 can include volatile memory 1110 and non-volatile memory 1112, which can employ one or more of the disclosed memory architectures, in various embodiments. The basic input/output system (BIOS), containing the basic routines to transfer information between elements within the computer 1102, such as during start-up, can be stored in non-volatile memory 1112. In addition, according to present innovations, codec 1135 can include at least one of an encoder or decoder, wherein the at least one of an encoder or decoder can consist of hardware, software, or a combination of hardware and software. Although, codec 1135 is depicted as a separate component, codec 1135 can be contained within non-volatile memory 1112. By way of illustration, and not limitation, non-volatile memory 1112 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1112 can employ one or more of the disclosed memory devices, in at least some embodiments. Moreover, non-volatile memory 1112 can be computer memory (e.g., physically integrated with computer 1102 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1110 can include random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1102 can also include removable/non-removable, volatile/non-volatile computer storage medium. FIG. 11 illustrates, for example, disk storage 1114. Disk storage 1114 can include, but is not limited to, devices like a magnetic disk drive, solid state disk (SSD), flash memory card, or memory stick. In addition, disk storage 1114 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1114 to the system bus 1108, a removable or non-removable interface can typically be used, such as interface 1116. It is appreciated that disk storage 1114 can store information related to an entity. Such information might be stored at or provided to a server or to an application running on an entity device. In one embodiment, the entity can be notified (e.g., by way of output device(s) 1136) of the types of information that can be stored to disk storage 1114 or transmitted to the server or application. The entity can be provided the opportunity to opt-in or opt-out of having such information collected or shared with the server or application (e.g., by way of input from input device(s) 1128).

It is to be appreciated that FIG. 11 describes software that can act as an intermediary between entities and the basic computer resources described in the operating environment 1100. Such software includes an operating system 1118. Operating system 1118, which can be stored on disk storage 1114, can act to control and allocate resources of the computer 1102. Applications 1120 can take advantage of the management of resources by operating system 1118 through program modules 1124, and program data 1126, such as the boot/shutdown transaction table and the like, that can be stored either in system memory 1106 or on disk storage 1114. It is to be appreciated that the claimed subject matter can be implemented with various operating systems or combinations of operating systems.

An entity can enter commands or information into the computer 1102 through input device(s) 1128. Input devices 1128 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1104 through the system bus 1108 via interface port(s) 1130. Interface port(s) 1130 can include, for example, a serial port, a parallel port, a game port, and a universal serial bus (USB). Output device(s) 1136 can use some of the same type of ports as input device(s) 1128. Thus, for example, a USB port can be used to provide input to computer 1102 and to output information from computer 1102 to an output device 1136. Output adapter 1134 is provided to illustrate that there are some output devices 1136 like monitors, speakers, and printers, among other output devices 1136, which can require special adapters. The output adapter 1134 can include, by way of illustration and not limitation, video and sound cards that can provide a means of connection between the output device 1136 and the system bus 1108. It should be noted that other devices or systems of devices can provide both input and output capabilities such as remote computer(s) 1138.

Computer 1102 can operate in a networked environment using logical connections to one or more remote computers, such as remote computer(s) 1138. The remote computer(s) 1138 can be a personal computer, a server, a router, a network PC, a workstation, a microprocessor based appliance, a peer device, a smart phone, a tablet, or other network node, and typically includes many of the elements described relative to computer 1102. For purposes of brevity, only a memory storage device 1140 is illustrated with remote computer(s) 1138. Remote computer(s) 1138 can be logically connected to computer 1102 through a network interface 1142 and then connected via communication connection(s) 1144. Network interface 1142 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1144 refers to the hardware/software employed to connect the network interface 1142 to the system bus 1108. While communication connection 1144 is shown for illustrative clarity inside computer 1102, it can also be external to computer 1102. The hardware/software necessary for connection to the network interface 1142 can include, for exemplary purposes only, internal and external technologies such as, modems including regular telephone grade modems, cable modems and DSL modems, ISDN adapters, and wired and wireless Ethernet cards, hubs, and routers.

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device, comprising:
    a memory; and
    a storage component operatively coupled to the memory and having one or more recesses to receive a second device to be charged by the storage component, wherein the storage component comprises:
        a charging circuit; and
        an inductive circuit coupled to the charging circuit, wherein the storage component harvests energy from one or more energy sources to charge the charging circuit and wherein, based on the energy harvested, the inductive circuit inductively couples to the second device having a second inductive circuit and positioned in at least one of the recesses and charges a power source of the second device, wherein the storage component further comprises a sterilization component that exposes the second device to a sterilizing agent, and wherein the sterilizing agent is selected from the group consisting of ultraviolet radiation, thermal radiation, and chemical solution.

2. The device of claim 1, further comprising an energy harvesting component coupled to the storage component and that harvests energy from the one or more energy sources, wherein the energy harvesting component is selected from the group consisting of a solar cell, a radio frequency antenna, a thermo-generator, and a microgenerator.

3. The device of claim 1, wherein the one or more energy sources is selected from the group consisting of magnetic energy, electric energy, electromagnetic radiant energy, solar energy, ultrasonic energy, thermal energy, kinetic energy, wind energy, light energy, and ambient energy.

4. The device of claim 1, wherein the memory stores computer executable components and the device further comprises a processor that executes computer executable components stored in the memory, wherein the computer executable components comprise:
    a data logging component that records data received from the second device; and a data communication component that facilitates communication of the data from a transmitter of the device over a network to one or more remote entities.

5. The device of claim 4, wherein the one or more remote entities is selected from the group consisting of a smart phone, a mobile device, and a server.

6. The device of claim 1, wherein at least one of the one or more recesses comprises a magnetic component that magnetically couples to the second device having a second magnetic component and wherein, based on the magnetic coupling, the magnetic component attracts the second magnetic component to position the second device in at least one of the one or more recesses such that the inductive circuit aligns axially with the second inductive circuit, thereby facilitating improved inductive coupling.

7. The device of claim 1, wherein the storage component further comprises an inductive coil coupled to the inductive circuit and integrated around or on a surface of at least one of the one or more recesses, thereby facilitating improved inductive coupling and improved charging efficiency associated with charging the power source.

8. The device of claim 1, wherein the storage component further comprises a communication circuit that communicatively couples to a second communication circuit of the second device, wherein the communication circuit receives data from the second communication circuit and wherein the communication circuit transmits the data.

9. A computer-implemented method, comprising:
harvesting energy, by a storage device comprising a processor, from one or more energy sources;
charging, by the storage device, a circuit coupled to the storage device based on harvested energy, wherein the circuit is coupled to an inductive coil;
charging, by the storage device, a power source of a second device based on inductively coupling, by the storage device, the inductive coil of the storage device with a second inductive coil of the second device; and
exposing, by the storage device, the second device to a sterilizing agent, wherein the sterilizing agent is selected from the group consisting of ultraviolet radiation, thermal radiation, and chemical solution.

10. The computer-implemented method of claim 9, wherein the one or more energy sources is selected from the group consisting of magnetic energy, electric energy, electromagnetic radiant energy, solar energy, ultrasonic energy, thermal energy, kinetic energy, wind energy, light energy, and ambient energy.

11. The computer-implemented method of claim 9, further comprising:
logging, by the storage device, data received from the second device; and
transmitting the data, by the storage device, over a network to one or more remote entities.

12. The computer-implemented method of claim 9, further comprising magnetically coupling, by the storage device, the storage device to the second device, thereby facilitating improved inductive coupling.

13. A system, comprising:
a first device having an inductive circuit;
a second device having a storage component that comprises a second inductive circuit that inductively couples to the inductive circuit of the first device and comprising:
a recess that receives the first device to be charged by the storage component, wherein the storage component comprises a charging circuit that is charged based on harvested energy by the storage component from one or more energy sources, and wherein the inductive coupling between the inductive circuit and the second inductive circuit charges a power source of the first device; and
a magnetic component located on the first device, the recess comprising a second magnetic component and wherein, based on magnetic coupling between the magnetic component and the second magnetic component, the magnetic component attracts the second magnetic component to position the first device in the recess such that the inductive circuit aligns axially with the second inductive circuit.

14. The system of claim 13, wherein the second device further comprises at least one of a solar cell or a radio frequency antenna coupled to the storage component and that harvests the energy.

15. The system of claim 13, wherein the first device is selected from the group consisting of a fingernail sensor, a contact lens, a finger ring sensor, and a wearable sensor.

16. The system of claim 13, further comprising a memory that stores computer executable components and a processor that executes the computer executable components stored in the memory, wherein the computer executable components comprise a data logging component that records data received from the first device.

17. The system of claim 16, wherein the data comprises health information associated with a wearer of the first device and the first device is selected from the group consisting of a fingernail sensor, a contact lens, a finger ring sensor, and a wearable sensor.

* * * * *